(12) United States Patent
Aicher et al.

(10) Patent No.: US 7,678,794 B2
(45) Date of Patent: Mar. 16, 2010

(54) POTENTIATORS OF GLUTAMATE RECEPTORS

(75) Inventors: Thomas Daniel Aicher, Superior, CO (US); Guillermo S. Cortez, Indianapolis, IN (US); Todd Michael Groendyke, Ann Arbor, MI (US); Albert Khilevich, Westfield, IN (US); James Allen Knobelsdorf, Fishers, IN (US); Fredrik Pehr Marmsater, Longmont, CO (US); Jeffrey Michael Schkeryantz, Fishers, IN (US); Tony Pisal Tang, Longmont, CO (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/718,742

(22) PCT Filed: Nov. 15, 2005

(86) PCT No.: PCT/US2005/041440

§ 371 (c)(1),
(2), (4) Date: May 7, 2007

(87) PCT Pub. No.: WO2006/057869

PCT Pub. Date: Jun. 1, 2006

(65) Prior Publication Data

US 2008/0004321 A1    Jan. 3, 2008

Related U.S. Application Data

(60) Provisional application No. 60/630,060, filed on Nov. 22, 2004.

(51) Int. Cl.
*A61K 31/50*    (2006.01)
*C07D 209/54*    (2006.01)
(52) U.S. Cl. .................. 514/247; 514/381; 548/408
(58) Field of Classification Search .............. 514/247, 514/381, 408; 544/358; 548/250, 255, 262, 548/2, 300, 1, 400
See application file for complete search history.

(56) References Cited

U.S. PATENT DOCUMENTS 4,853,398 A    8/1989    Carr et al.
5,977,177 A    11/1999   Englert et al.
6,194,432 B1   2/2001    Sheftell et al.
6,686,382 B2 * 2/2004    Wu et al. .................. 514/380

FOREIGN PATENT DOCUMENTS

| EP | 0028063 | 6/1984 |
|---|---|---|
| EP | 0174770 | 3/1986 |
| EP | 0288189 | 10/1988 |
| EP | 0516069 | 12/1992 |
| JP | 61-130271 | 6/1986 |
| WO | WO0156990 | 8/2001 |
| WO | WO2004018386 | 3/2004 |
| WO | WO2006014918 | 2/2006 |
| WO | WO2006015158 | 2/2006 |
| WO | WO2006049968 | 5/2006 |
| WO | WO2006/005860 A1 | 6/2006 |
| WO | WO2006/057870 A1 | 6/2006 |

OTHER PUBLICATIONS

Brown et al., Hydroxyacetophenone-Derived Antagonists of the Peptidoleukotrienes, *J. Med. Chem.*, 1989, 807-826, 32.
Pinkerton et al., Allosteric potentiators of the metabotropic glutamate receptor 2 (mGlu2). Part 1: Identification and synthesis of phenyl-tetrazolyl acetophenones, *Bioorganic & Medicinal Chemistry Letters*, 2004, 5329-5332, 14.
Pinkerton et al., Allosteric potentiators of the mteabotropic glutamate receptor 2 (mGlu2). Part 2: 4-Thiopyridyl acetophenones as non-tetrazole containing mGlu2 receptor potentiators, *Bioorganic & Medicinal Chemistry Letters*, 2004, 5867-5872, 14.

* cited by examiner

*Primary Examiner*—Golam M Shameem
*Assistant Examiner*—Susannah Chung
(74) *Attorney, Agent, or Firm*—Mark A. Winter

(57) ABSTRACT

The present invention provides a compound of formula (I): pharmaceutical compositions thereof, and methods of using the same, processes for preparing the same, and intermediates thereof.

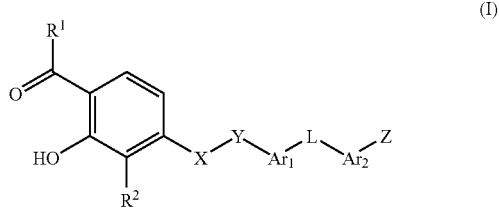

(I)

19 Claims, No Drawings

POTENTIATORS OF GLUTAMATE RECEPTORS

This application is a United States national phase entry, pursuant to 35 U.S.C. 371, of PCT/US2005/041440, filed Nov. 15, 2005, which claims the benefit of U.S. provisional application Ser. No. 60/630,060, filed Nov. 22, 2004.

The present invention provides a compound of formula I, pharmaceutical compositions thereof, and methods of using the same, as well as processes for preparing the same, and intermediates thereof.

BACKGROUND OF THE INVENTION

The excitatory amino acid L-glutamate (at times referred to herein simply as glutamate) through its many receptors mediates most of the excitatory neurotransmission within the mammalian central nervous system (CNS) and has been implicated in numerous peripheral nervous system (PNS) pathways. The excitatory amino acids, including glutamate, are of great physiological importance, playing a role in a variety of neurological, physiological and psychiatric processes, such as synaptic plasticity, motor control, respiration, cardiovascular regulation, sensory perception, and emotional responses.

Glutamate acts via at least two distinct classes of receptors. One class is composed of the ionotropic glutamate (iGlu) receptors that act as ligand-gated ion channels. Via activation of the iGlu receptors, glutamate is thought to regulate fast neuronal transmission within the synapse of two connecting neurons in the CNS. The second general type of receptor is the G-protein or second messenger-linked "metabotropic" glutamate (mGlu) receptor. Both types of receptors appear not only to mediate normal synaptic transmission along excitatory pathways, but also participate in the modification of synaptic connections during development and throughout life. Schoepp, Bockaert, and Sladeczek, Trends in Pharmacol. Sci., 11, 508 (1990); McDonald and Johnson, Brain Research Reviews, 15, 41 (1990).

The mGlu receptors belong to the Class C G-protein coupled receptor (GPCR) family. This family of GPCR's, including the calcium-sensing receptors, $GABA_B$ receptors and sensory receptors, are unique in that effectors bind to the amino-terminus portion of the receptor protein translating a signal via the transmembrane segments to the intracellular matrix through receptor/G-protein interactions. Ozawa, Kamiya and Tsuzuski, Prog. Neurobio., 54, 581 (1998). It has been demonstrated that the receptors are localized either pre- and/or post-synapticly where they can regulate neurotransmitter release, either glutamate or other neurotransmitters, or modulate the post-synaptic response of neurotransmitters, respectively.

At present, there are eight mGlu receptors that have been positively identified, cloned, and their sequences reported. These are further subdivided based on their amino acid sequence homology, their ability to effect certain signal transduction mechanisms, and their known pharmacological properties. Ozawa, Kamiya and Tsuzuski, Prog. Neurobio., 54, 581 (1998). For instance, the Group I mGlu receptors, which include the mGlu1 and mGlu5, are known to activate phospholipase C (PLC) via $G\alpha q$-proteins thereby resulting in the increased hydrolysis of phosphoinositides and intracellular calcium mobilization. There are several compounds that are reported to activate the Group I mGlu receptors including DHPG, (+/−)-3,5-dihydroxyphenylglycine. Schoepp, Goldworthy, Johnson, Salhoff and Baker, J. Neurochem., 63, 769 (1994); Ito, et al., Neurorep., 3, 1013 (1992). The Group II mGlu receptors consist of the two distinct receptors, mGlu2 and mGlu3 receptors. Both receptors are negatively coupled to adenylate cyclase via activation of $G\alpha i$-protein. These receptors can be activated by a group-selective compound such as (1S,2S,5R,6S)-2-aminobicyclo[3.1.0]hexane-2,6-dicarboxylate. Monn, et al., J. Med. Chem., 40, 528 (1997); Schoepp, et al., Neuropharmacol., 36, 1 (1997). Similarly, the Group III mGlu receptors, including mGlu4, mGlu6, mGlu7 and mGlu8, are negatively coupled to adenylate cyclase via $G\alpha i$ and are potently activated by L-AP4 (L-(+)-2-amino-4-phosphonobutyric acid). Schoepp, Neurochem. Int., 24, 439 (1994).

It should be noted that many of the available pharmacological tools are not ideal in that they cross react not only on the receptors within a group of mGlu receptors but also often have some activity between groups of mGlu receptors. For instance, compounds such as 1S,3R-ACPD, (1S,3R)-1-aminocyclopentane-trans-1,3-dicarboxylic acid, are believed to activate all of the Group I, II and III mGlu receptors depending upon the dose utilized while others, such as 1S,3S-ACPD, (1S,3S)-1-aminocyclopentane-trans-1,3-dicarboxylic acid, are more selective for the Group II receptors (mGlu2/3) than the Group I (mGlu1/5) or Group III (mGlu4/6/7/8). Schoepp, Neurochem. Int., 24, 439 (1994). To date, there are very few examples of selective agents for the mGlu receptors. Schoepp, Jane, and Monn, Neuropharmacol., 38, 1431 (1999).

It has become increasingly clear that there is a link between modulation of excitatory amino acid receptors, including the glutamatergic system, through changes in glutamate release or alteration in postsynaptic receptor activation, and a variety of neurological, psychiatric and neuroinflammatory disorders. e.g. Monaghan, Bridges and Cotman, Ann. Rev. Pharmacol. Toxicol., 29, 365-402 (1989); Schoepp and Sacann, Neurobio. Aging, 15, 261-263 (1994); Meldrum and Garthwaite, Tr. Pharmacol. Sci., 11, 379-387 (1990). The medical consequences of such glutamate dysfunction make the abatement of these neurological processes an important therapeutic goal.

Leukotrienes are potent local mediators, playing a major role in inflammatory and allergic responses including arthritis, asthma, psoriasis, and thrombotic disease. Leukotrienes are straight chain eicosanoids produced by the oxidation of arachidonic acid by lipoxygenases in several cell types including: eosinophils, neutrophils, mast cells, leukocytes, and macrophages. At the present time, there are two established Class A GPCR receptors for the cysteinyl-leukotrienes (CysLT1 and CysLT2) which the leukotrienes LTC4, LTD4 and LTE4 activate, mediating their proinflammatory effects. Each of the CysLT receptors has distinct tissue distributions and associations with physiological responses. Also, the leukotriene LTD4 has a higher affinity for the CysLT1 receptor than the other leukotrienes. Back, M. Life Sciences 71, 611-622, (2002). The leukotrienes, especially LTD4 and its receptor CysLT1, have been implicated in the pathogenesis of airway and allergic diseases such as asthma by contributing to bronchoconstriction, mucus secretion, and eosinophil migration. Thus, leukotrienes have been shown to play an important role in the pathology of asthma. Rigorous proof for the role of leukotrienes in asthma has been provided by several pivotal clinical trials in which orally administered LTD4 receptor antagonists produce clear therapeutic benefit in asthma patients. These benefits include reduction in the use of classic asthma therapies such as corticosteroids. Kemp, J. P., Amer. J. Resp. Medi. 2, 139-156, (2003).

Numerous investigations confirm the importance of the leukotrienes in allergic disorders as well. Thus, after allergen provocation, a marked increase in the LT concentration in the nasal lavage fluid of patients with allergic rhinitis was detected both in the early phase and in the late phase. Creticos, P. S., S. P. Peters, N. F. Adkinson, R. M. Naclerio, E. C. Hayes, P. S. Norman, L. M. Lichtenstein, N. Eng. J. Med. 310:1626 (1984). In addition, treatment with clinically efficacious antihistamines, such as azelastine, has shown a reduction in the formation of the cysteinyl-leukotrines, establishing a correlative relationship of allergic reaction symptoms to the degree of leukotriene formation and, thus, CysLT receptor activation. Achterrath-Tuckermann, U., Th. Simmet, W. Luck, I. Szelenyi, B. A. Peskar, Agents and Actions 24:217, 1988; Shin, M. H., F. M. Baroody, D. Proud, A. Kagey-Sobotka, L. M. Lichtenstein, M. Naclerio, Clin. Exp. Allergy 22:289, 1992.

U.S. Pat. No. 6,194,432 B1 discloses a method for using leukotriene antagonist drugs to prevent and treat recurrent primary headaches including migraine headaches.

U.S. Pat. No. 5,977,177 discloses certain substituted phenyl derivative compounds are modulators of endothelin and, as such, are useful in treating many different conditions including asthma.

U.S. Pat. No. 4,853,398 discloses certain benzene derivative compounds are selective antagonists of leukotrienes and, as such, are useful in treating allergic disorders such as asthma.

European Patent Application No. EP 28063 A1 and UK Patent Application No. GB 2058785 disclose certain phenol derivative compounds are antagonists of slow reacting substance of anaphylaxis and, as such, are useful in treating asthma, hay fever and skin afflictions.

Brown, F. J. et al *J. Med. Chem.* 32, p. 807-826 (1989) discloses certain hydroxyacetophenone derivative compounds are antagonists of leukotrienes and, as such, play a role in treating asthma.

International Patent Application Publication No. WO 2001056990 A2 and U.S. Pat. No. 6,800,651 B2 disclose certain pyridine derivative compounds are potentiators of metabotropic glutamate receptor function, specifically; potentiators of mGlu2 receptor function and, as such, are useful in the treatment of many different conditions including anxiety and migraine headache.

International Patent Application Publication No. WO 2004018386 and Pinkerton, A. B. et al *Bioorg. Med. Chem. Lett.*, 14, p. 5329-5332 (2004) disclose certain acetophenone derivative compounds are potentiators of glutamate receptor function, specifically; potentiators of mGlu2 receptor function and, as such, are useful in the treatment of many different conditions including anxiety, schizophrenia and migraine headache.

Recently, Pinkerton, A. B. et al *Bioorg. Med. Chem. Lett.*, 14, p. 5867-5872 (2004) disclose certain 4-thiopyridyl acetophenone derivative compounds are potentiators of glutamate receptor function, specifically; potentiators of mGlu2 receptor function and, as such, may be useful in the treatment of CNS disorders including anxiety, schizophrenia and epilepsy.

The present invention provides compounds of formula I that are potentiators of the mGlu2 receptor and antagonists of the CysLT1 receptor. As such, compounds of formula I would provide a means to treat disorders associated with glutamate or leukotrienes. In addition, it is anticipated that in disorders with a glutamate and leukotriene component to the onset, propagation and/or symptoms, the compounds of formula I will provide an effective treatment for the patient. The medical consequences of such glutamate dysfunction make the abatement of these neurological processes an important therapeutic goal.

SUMMARY OF THE INVENTION

The present invention provides a compound of formula I:

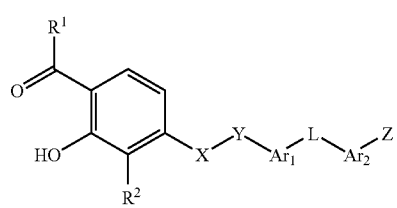

wherein $R^1$ is selected from the group consisting of C1-C5 alkyl, C3-C7 cycloalkyl, C4-C8 cycloalkylalkyl, phenyl and substituted phenyl;

$R^2$ is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazolyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl and substituted pyridazinyl;

X is selected from the group consisting of O, $S(O)_m$, and $NR^3$;

Y is selected from the group consisting of C1-C3 alkanediyl and substituted C1-C3 alkanediyl;

$Ar_1$ and $Ar_2$ are independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl;

L is selected from the group consisting of -G-$SO_2$N($R^3$)-J-, -G-($R^3$)N$SO_2$-J-, -G-C(=O)N($R^3$)-J-, -G-($R^3$)NC(=O)-J-, and -G-N($R^3$)C(=O)N($R^3$)-J-;

G and J are independently selected from the group consisting of a bond and C1-C3 alkanediyl;

$R^3$ is independently hydrogen or C1-C5 alkyl;

Z is selected from the group consisting of $(CH_2)_n$COOH,

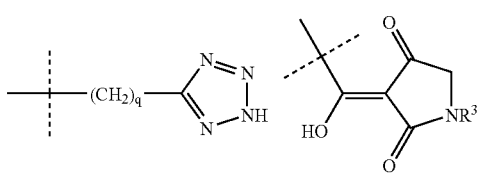

-continued

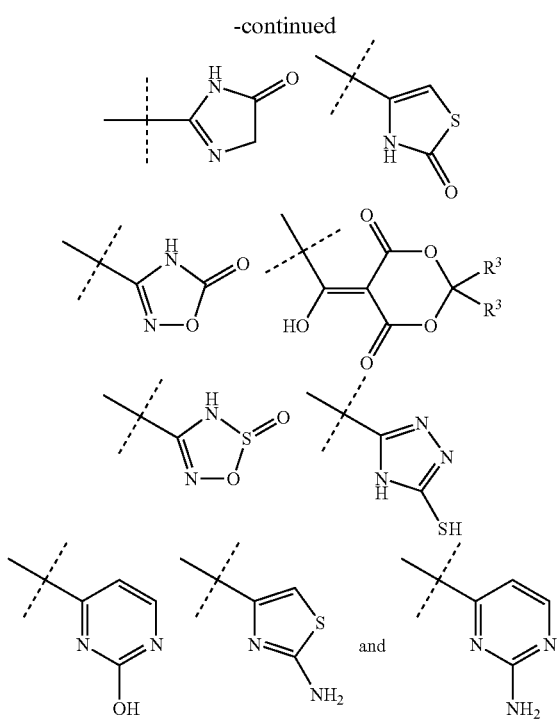

m is 0, 1, or 2;

n and q are independently 0, 1, 2 or 3;

provided Z is attached at 1-3 (meta) or 1-4 (para) position when $R^1$ is methyl, $R^2$ is propyl, $R^3$ is hydrogen, X is O, Y is –$CH_2$—, L is -G-($R^3$)NC(=O)-J-, G is a bond, J is a bond or —$CH_2$—, $Ar_1$ and $Ar_2$ are phenylene, Z is $(CH_2)_n$COOH and n is 0; and pharmaceutically acceptable salts thereof.

The present invention also provides for novel pharmaceutical compositions, comprising a compound of the formula I and a pharmaceutically acceptable diluent.

Because the compounds of formula I are potentiators of the mGlu2 receptor, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, multiple sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

In another embodiment the present invention provides methods of treating neurological and psychiatric disorders associated with glutamate dysfunction, comprising administering to a patient in need thereof an effective amount of a compound of formula I. That is, the present invention provides for the use of a compound of formula I or pharmaceutical composition thereof for the treatment neurological and psychiatric disorders associated with glutamate dysfunction.

Of the disorders above, the treatment of migraine, anxiety, schizophrenia, and epilepsy are of particular importance.

In a preferred embodiment the present invention provides a method for treating migraine, comprising administering to a patient in need thereof an effective amount of a compound of formula I.

In another preferred embodiment the present invention provides a method for treating anxiety, comprising administering to a patient in need thereof an effective amount of a compound of formula I. Particularly preferred anxiety disorders are generalized anxiety disorder, panic disorder, and obsessive compulsive disorder.

In another preferred embodiment the present invention provides a method for treating schizophrenia, comprising administering to a patient in need thereof an effective amount of a compound of formula I.

In yet another preferred embodiment the present invention provides a compound of formula I for use as a medicament.

In yet another preferred embodiment the present invention provides the use of a compound of formula I for the manufacture of a medicament for the treatment of migraine.

In yet another preferred embodiment the present invention provides the use of a compound of formula I for the manufacture of a medicament for the treatment of neurological and psychiatric disorders associated with glutamate dysfunction.

In yet another preferred embodiment the present invention provides a pharmaceutical composition for the treatment of neurological and psychiatric disorders associated with glutamate dysfunction containing as an active ingredient a compound of formula I.

In yet another preferred embodiment the present invention provides a method for treating epilepsy, comprising administering to a patient in need thereof an effective amount of a compound of formula I.

Because such potentiators, including the compounds of formula I, positively modulate metabotropic glutamate receptor response to glutamate, it is an advantage that the present methods utilize endogenous glutamate.

Because such potentiators positively modulate metabotropic glutamate receptor response to glutamate agonists it is understood that the present invention extends to the treatment of neurological and psychiatric disorders associated with glutamate dysfunction by administering an effective amount of a metabotropic glutamate potentiator, including the compounds of formula I, in combination with a potentiated amount of a metabotropic glutamate receptor agonist. Such a combination may be advantageous in that it may augment the activity and selectivity of an agonist of metabotropic glutamate receptors, in particular a potentiator of mGlu2 receptors.

Because many the compounds of formula I are antagonists of the CysLT1 receptor, many of the compounds of formula I are useful for the treatment of a variety of disorders mediated by one or more leukotrienes such as inflammatory and allergic disorders associated with leukotriene mediation including inflammatory bowel syndrome, inflammatory bowel disease, arthritis, asthma, psoriasis, and thrombotic disease.

In another embodiment the present invention provides methods of treating a variety of disorders mediated by one or more leukotrienes, comprising administering to a patient in need thereof an effective amount of a compound of formula I. That is, the present invention provides for the use of a compound of formula I or pharmaceutical composition thereof for the treatment inflammatory and allergic disorders associated with leukotriene mediation.

In a preferred embodiment the present invention provides a method for treating asthma, comprising administering to a patient in need thereof an effective amount of a compound of formula I.

In another embodiment the present invention provides a process for preparing a compound of formula I or a pharmaceutically acceptable salt thereof, as well as intermediate compounds thereof.

DETAILED DESCRIPTION OF THE INVENTION

This invention provides methods of potentiating metabotropic glutamate receptors, in particular mGlu2 receptors. In the present methods an effective amount of a potentiator of metabotropic glutamate 2 receptors, including a compound of formula I, is administered which positively modulates the effect of glutamate or glutamate agonists on the subject receptor.

Before describing the present invention in greater detail, it is understood that the invention in its broadest sense is not limited to particular embodiments described herein, as variations of the particular embodiments described herein are within the scope of the claimed invention.

Thus, compounds useful in the present invention are those which are potentiators of metabotropic glutamate receptors, particularly, those that potentiate the effects of glutamate and glutamate agonists at mGlu2 metabotropic glutamate receptors, and even more particularly, those that potentiate the effects of glutamate and glutamate agonists at mGlu2 receptors. Useful compounds are varied in structure, and so long as they embrace the above properties, they are suitable for use in the present invention. Preferred compounds include, but are not limited to, those described herein.

The compounds of formula I potentiate the function of glutamate receptors. Specifically, the compounds of formula I are potentiators of the mGlu2 receptor.

Compounds of in the present invention also include those which are modulators of leukotriene receptors, particularly, those that antagonize the CysLT1 receptor.

As used herein, the following terms have the meanings indicated:

The term "C1-C5 alkyl" refers to a straight or branched alkyl chain having from one to five carbon atoms, and includes methyl, ethyl, propyl, iso-propyl, butyl, iso-butyl, sec-butyl, t-butyl, pentyl and the like. Particular values of "C1-C5 alkyl" are methyl, ethyl, n-propyl and iso-propyl.

The term "alkyl" refers to a monovalent aliphatic hydrocarbon. Within the meaning of the term "alkyl" is the term "C1-C3 alkyl".

The term "C1-C3 alkyl" refers to a straight or branched alkyl chain having from one to three carbon atoms, and includes methyl, ethyl, propyl, iso-propyl, and the like.

The term "substituted C1-C5 alkyl" refers to a straight or branched alkyl chain having from one to five carbon atoms, and includes methyl, ethyl, propyl, iso-propyl, butyl, iso-butyl, sec-butyl, t-butyl and pentyl having from 1 to 3 substituents selected from the group consisting of hydroxy, halogen, azido, alkoxy, acyloxy, carboxy, alkoxycarbonyl, amido, substituted amido, amino, acylamino, sulfonylamido, sulfonamide, phenyl, substituted phenyl, phenoxy, substituted phenoxy, benzyloxy, substituted benzyloxy, pyridyl, substituted pyridyl, thienyl, and substituted thienyl.

The term "C1-C5 alkanediyl" refers to a straight or branched divalent alkyl chain having from one to five carbon atoms, and includes methylene and ethane-1,1-diyl.

The term "substituted C1-C5 alkanediyl" refers to a straight or branched divalent alkyl chain having from one to five carbon atoms, and includes methylene having a substituent selected from the group consisting of hydroxyl, fluoro, azido, methoxy, amino, acetylamino and methylsulfonamide.

The term "C1-C3 alkanediyl" refers to a straight or branched divalent alkyl chain having from one to three carbon atoms, and includes methylene.

The term "substituted C1-C3 alkanediyl" refers to a straight or branched alkyl chain having from one to three carbon atoms, and includes methylene, having from 1 or 2 substituents selected from the group consisting of hydroxy, halogen, azido, alkoxy, acyloxy, carboxy, alkoxycarbonyl, amido, substituted amido, amino, acylamino, sulfonylamido, sulfonamide, phenyl, substituted phenyl, pyridyl, substituted pyridyl, thienyl, and substituted thienyl.

The term "halogen or halo" refers to chloro, fluoro, bromo or iodo.

The term "C1-C3 fluoroalkyl" refers to an alkyl chain having from one to three carbon atoms substituted with one or more fluorine atoms, and includes fluoromethyl, difluoromethyl, trifluoromethyl, 2,2,2-trifluoroethyl, 3,3,3-trifluoropropyl and the like. A particular value of "C1-C3 fluoro alkyl" is trifluoromethyl.

The term "C1-C4 alkoxy" refers to straight or branched alkyl chain having from one to four carbon atoms attached to an oxygen atom, and includes methoxy, ethoxy, propoxy, iso-propoxy, butoxy, iso-butoxy, sec-butoxy, t-butoxy, and the like.

The term "substituted C1-C4 alkoxy" refers to straight or branched alkyl chain having from one to four carbon atoms attached to an oxygen atom, and includes methoxy, ethoxy, propoxy, iso-propoxy, butoxy, iso-butoxy, sec-butoxy, t-butoxy, and the like, having from 1 to 3 substituents selected from the group consisting of hydroxy, halogen, alkoxy, carboxy, amido, substituted amido, amino, acylamino, sulfonylamido, sulfonamide, phenyl, and substituted phenyl; and when one or more of the substituents is hydroxy, halogen, alkoxy, amino, acylamino, and sulfonamide, then those substituents are not attached to the same carbon as the alkoxy oxygen atom.

The term "C3-C7 cycloalkyl" refers to saturated cyclic alkyl group having from three to seven carbon atoms and includes cyclopropyl, cyclobutyl, cyclopentyl, cyclohexyl, and cycloheptyl.

The term "C4-C8 cycloalkylalkyl" refers to saturated cyclic alkyl group having from three to seven carbon atoms linked to the point of substitution by a divalent unsubstituted saturated straight-chain or branched-chain hydrocarbon radical having at least 1 carbon atom and includes, cyclopropylmethyl, cyclopropyl-2-propyl, cyclobutylethyl, cyclopentylmethyl, cyclohexylmethyl, cycloheptylmethyl and the like.

The terms "phenyl and substituted phenyl" or "phenylene and substituted phenylene" refer to a monovalent or divalent radical, respectively, of the formula

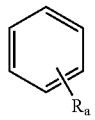

wherein $R_a$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. Particular values of $R_a$ are hydrogen and fluoro.

The terms "thiophenyl and substituted thiophenyl" or "thiophenediyl and substituted thiophenediyl" refer to a monovalent or divalent radical, respectively, of the formula

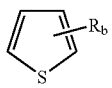

wherein $R_b$ is from 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_b$ is hydrogen.

The terms "pyridinyl and substituted pyridinyl" or "pyridinediyl and substituted pyridinediyl" refer to a monovalent or divalent radical, respectively, of the formula

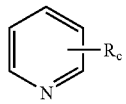

wherein $R_c$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_c$ is hydrogen.

The terms "thiazolyl and substituted thiazolyl" or "thiazolediyl and substituted thiazolediyl" refer to a monovalent or divalent radical, respectively, of the formula

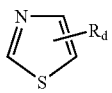

wherein $R_d$ is from 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_d$ is hydrogen.

The terms "furanyl and substituted furanyl" or "furanediyl and substituted furanediyl" refer to a monovalent or divalent radical, respectively, of the formula

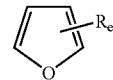

wherein $R_e$ is from 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_e$ is hydrogen.

The terms "isothiazolyl and substituted isothiazoyl" or "isothiazolediyl and substituted isothiazolediyl" refer to a monovalent or divalent radical, respectively, of the formula

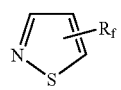

wherein $R_f$ is from 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_f$ is hydrogen.

The terms "isoxazolyl and substituted isoxazolyl" or "isoxazolediyl and substituted isoxazolediyl" refer to a monovalent or divalent radical, respectively, of the formula

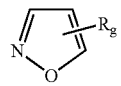

wherein $R_g$ is from 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_g$ is hydrogen.

The terms "1,2,4-oxadiazolyl and substituted 1,2,4-oxadiazolyl" or "1,2,4-oxadiazole-3,5-diyl" refer to a monovalent radical or divalent radical lacking $R_h$, respectively, of the formula

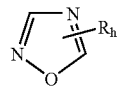

wherein $R_h$ is independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_h$ is hydrogen.

The terms "pyrimidinyl and substituted pyrimidinyl" or "pyrimidinediyl and substituted pyrimidinediyl" refer to a monovalent or divalent radical, respectively, of the formula

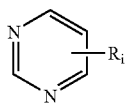

wherein $R_i$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_i$ is hydrogen.

The terms "pyridazinyl and substituted pyridazinyl" or "pyridazinediyl and substituted pyridazinediyl" refer to a monovalent or divalent radical, respectively, of the formula

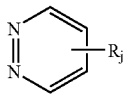

wherein $R_j$ is from 1 to 3 groups independently selected from the group consisting of hydrogen, hydroxy, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_j$ is hydrogen.

The terms "oxazolyl and substituted oxazolyl" or "oxazolediyl and substituted oxazolediyl" refer to a monovalent or divalent radical, respectively, of the formula

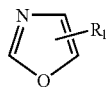

wherein $R_l$ is from 1 or 2 groups independently selected from the group consisting of hydrogen, alkyl, substituted alkyl, cycloalkyl, alkoxy, substituted alkoxy, halogen, carboxy, alkoxycarbonyl, amido, substituted amido, amino, acylamino, sulfonylamido, sulfonamide, cyano, nitro, phenyl, and substituted phenyl. A particular value of $R_l$ is hydrogen.

The term "carboxy" refers to a radical of the formula

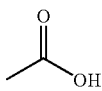

The term "alkoxycarbonyl" refers to a radical of the formula

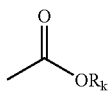

wherein $R_k$ is selected from the group consisting of alkyl, substituted alkyl, phenyl and substituted phenyl. Particular values of $R_k$ are methyl and ethyl.

The term "amido" refers to a radical of the formula

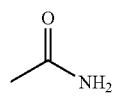

The term "substituted amido" refers to a radical of the formula

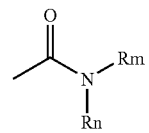

wherein $R_m$ is selected from the group consisting of alkyl and $R_n$ is selected from the group consisting of hydrogen, alkyl, phenyl and substituted phenyl. A particular value for $R_m$ is methyl. Particular values for $R_n$ are hydrogen and methyl.

The term "acylamino" refers to a radical of the formula

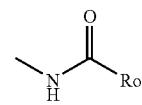

wherein $R_o$ is selected from the group consisting of alkyl, phenyl, and substituted phenyl. A particular value of $R_o$ is methyl.

The term "sulfonylamido" refers to a radical of the formula

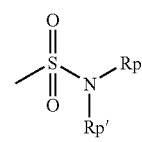

wherein $R_p$ is selected from the group consisting of alkyl, phenyl, and substituted phenyl; and $R_{p'}$ is selected from the group consisting of hydrogen and alkyl. A particular value for $R_p$ is methyl. Particular values for $R_{p'}$ are hydrogen and methyl.

The term "sulfonamide" refers to a radical of the formula

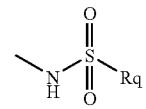

wherein $R_q$ is selected from the group consisting of alkyl, phenyl, and substituted phenyl. A particular value of $R_q$ is methyl.

As is readily apparent to those skilled in the art, the compounds of formula I may exist as tautomers. Where tautomers exist, each tautomeric form and mixtures thereof, are contemplated as included in the present invention. When any reference in this application to one of the specific tautomers of the compounds of formula I is given, it is understood to encompass every tautomeric form and mixtures thereof. For example, where the group Z is tetrazolyl, a compound of formula I exists as tautomer I and tautomer II. As such, it is understood any reference to a compound of formula I where the group Z is tetrazolyl as tautomer I encompasses tautomer II as well as mixtures of tautomer I and tautomer II.

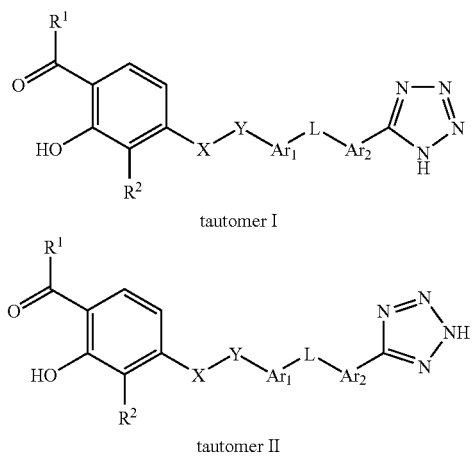

tautomer I tautomer II

It is understood that compounds of the present invention may exist as stereoisomers. All enantiomers, diastereomers, and mixtures thereof, are contemplated within the present invention. Where specific stereochemistries are identified in this application, the Cahn-Ingold-Prelog designations of (R)- and (S)- and the cis- and trans-designation of relative stereochemistry are used to refer to specific isomers and relative stereochemistry. Known optical rotations are designated by (+) and (−) for dextrorotatary and levorotatary, respectively. Where a chiral compound is resolved into its enantiomers, but absolute configurations are not determined and thus unknown, the isomers are designated as isomer 1, isomer 2, etc.

Specific stereoisomers can be prepared by stereospecific synthesis using enantiomerically pure or enriched starting materials. The specific stereoisomers of either starting materials or compounds of formula I can be resolved by techniques well known in the art, such as those found in *Stereochemistry of Organic Compounds*, E. I. Eliel and S. H. Wilen (Wiley 1994) and *Enantiomers, Racemates, and Resolutions*, J. Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts.

While all enantiomers, diastereomers, and mixtures thereof, are contemplated within the present invention, preferred embodiments are single enantiomers and single diastereomers.

The terms "$Ar_1$ and $Ar_2$" refer to five or six member aryl or heterocyclic rings independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl. It is understood that $Ar_1$ and $Ar_2$ being at least bi-radical may be attached in a 1-2, 1-3 or 1-4 regioisomeric position depending on the nature of the ring and the number and location of substituents. It is further understood that the present invention encompasses all possible regioisomeric combinations of attachment to $Ar_1$ and $Ar_2$. For example, where $Ar_1$ is phenylene there exists three possible regioisomers, designated as 1-2 (ortho or o-), 1-3 (meta or m-) and 1-4 (para or p-), all of which are encompassed in the present invention for a compound of formula I where $Ar_1$ is phenylene.

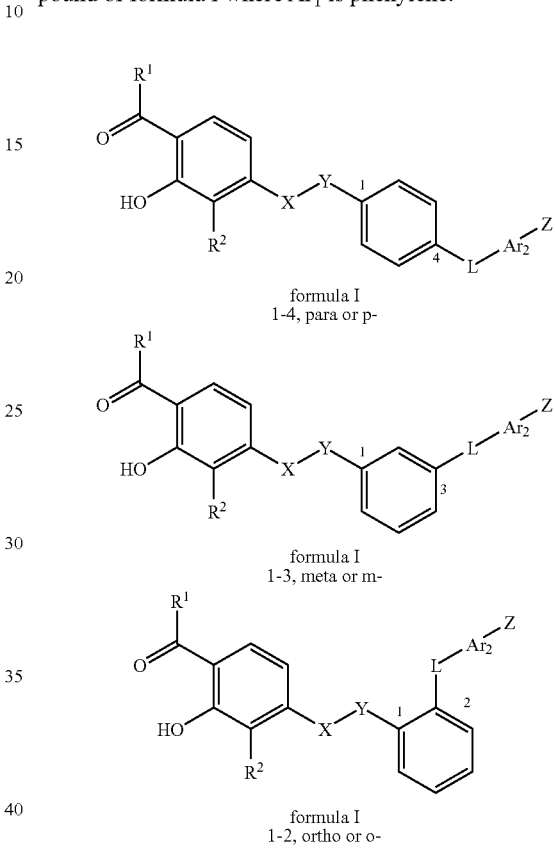

formula I
1-4, para or p- formula I
1-3, meta or m- formula I
1-2, ortho or o-

The term "pharmaceutically acceptable salt" refers to an addition salt that exists in conjunction with the acidic and/or basic portion of a compound of formula I. Such salts include the pharmaceutically acceptable salts listed in *Handbook of Pharmaceutical Salts: Properties, Selection and Use*, P. H. Stahl and C. G. Wermuth (Eds.), Wiley-VCH, New York, 2002 which are known to the skilled artisan. Pharmaceutically acceptable salts that are acid addition are formed when a compound of formula I and the intermediates described herein containing a basic functionality are reacted with a pharmaceutically acceptable acid. Pharmaceutically acceptable acids commonly employed to form such acid addition salts include inorganic acids, such as hydrochloric, hydrobromic, nitric, sulphuric or phoshoric acids, and organic acids such as acetic, citric, esylic, fumaric, glycolic, glucuronic, glutaric, lactic, maleic, malic, mandelic, mesylic, napadisylic, oxalic, succinic, tartaric, salicyclic, o-acetoxybenzoic, or p-toluene-sulphonic. Pharmaceutically acceptable salts that are base addition are formed when a compound of formula I and the intermediates described herein containing a acidic functionality are reacted with a pharmaceutically acceptable base. Pharmaceutically acceptable bases commonly employed to form base addition salts include organic bases such as ammonia, arginine, benethamine, benzathine, benzylamine, betaine, butylamine, choline, dicyclohexylamine, diethanolamine, diethylamine, ethylenediamine, glucosamine, imidazole, lysine, piperazine, procaine, and inorganic bases such as calcium, potassium, sodium and zinc salts of hydroxide, carbonate or bicarbonate and the like.

In addition to pharmaceutically acceptable salts, other salts are included in the invention. They may serve as intermediates in the purification of compounds or in the preparation of other, for example pharmaceutically-acceptable, acid addition salts, or are useful for identification, characterization or purification.

The term "protecting group or Pg," as used herein, refers to those groups intended to protect or block functional groups against undesirable reactions during synthetic procedures. In the case of an amino or hydroxyl functional group, the suitable protecting group used will depend upon the conditions that will be employed in subsequent reaction steps wherein protection is required. For example, it may be desirable to employ the protection of multiple functional groups, such as amino and hydroxyl, and control their protection and deprotection independently. Commonly used amino and hydroxyl protecting groups are disclosed in *Protective Groups In Organic Synthesis*, T. W. Greene and P. G. M. Wuts 3rd Ed. (John Wiley & Sons, New York (1999)). Suitable amino protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like, carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha, alpha-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable amino protecting groups are acetyl, methyloxycarbonyl, benzoyl, pivaloyl, allyloxycarbonyl, t-butylacetyl, benzyl, t-butyloxycarbonyl (Boc) and benzyloxycarbonyl (Cbz). Suitable hydroxyl protecting groups include ethers such as methoxymethyl, 1-ethoxyethyl, tert-butyl, allyl, benzyl, tetrahydropyranyl and the like; silyl ethers such as trimethylsilyl, triethylsilyl, triisopropylsilyl, tert-butyldimethylsilyl and the like; esters such as formate, acetate, pivaloate, benzoate and the like; and sulfonates such as mesylate, benzylsulfonate, tosylate and the like. Preferred suitable hydroxyl protecting groups are acetyl, trimethylsilyl, triisopropylsilyl, tert-butyldimethylsilyl and benzyl.

As with any group of pharmaceutically active compounds, some groups are preferred in their end use application. Preferred embodiments for a compound of formula I of the present invention are given below.

Compounds in which $R^1$ is C1-C5 alkyl are preferred.
Compounds in which $R^1$ is methyl are more preferred.
Compounds in which $R^2$ is C1-C5 alkyl are preferred.
Compounds in which $R^2$ is propyl are more preferred.
Compounds in which X is O are preferred.
Compounds in which Y is C1-C3 alkanediyl are preferred.
Compounds in which Y is methylene are more preferred.
Compounds in which $Ar_1$ and $Ar_2$ are independently phenylene or pyridinediyl are preferred.
Compounds in which $Ar_1$ is phenylene are preferred.
Compounds in which $Ar_1$ is phenylene or pyridinediyl are preferred. Compounds in which $Ar_1$ is phenylene or pyridinediyl, either attached in the 1-3 position, are more preferred. Compounds in which $Ar_1$ is phenylene or pyridinediyl, either ring attached in the 1-4 position, are even more preferred.
Compounds in which $Ar_2$ is substituted phenylene are preferred. More specifically, compounds in which $Ar_2$ is fluorophenylene are preferred. Compounds in which $Ar_2$ is phenylene are more preferred.
Compounds in which $Ar_2$ is attached at the 1-4 position are preferred.
Compounds in which $Ar_2$ is attached at the 1-3 position are preferred.
Compounds in which $Ar_1$ is attached at the 1-3 or 1-4 position are preferred.
Compounds in which L is —SO$_2$NH—, —NHSO$_2$—, —C(=O)NH—, —NHC(=O)—, or —NHC(=O)NH— are preferred.
Compounds in which Z is

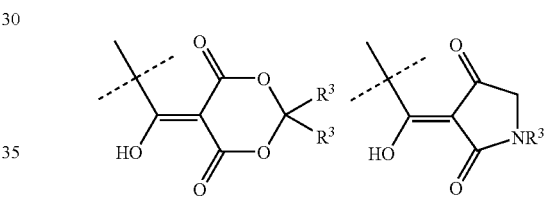

are preferred. Compounds in which Z is

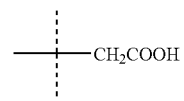

are more preferred. Compounds in which Z is

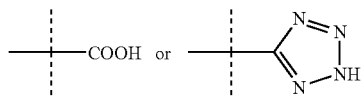

are even more preferred.
Compounds of formula I in which
$R^1$ is methyl;
$R^2$ is propyl;
X is O;
Y is methylene;
$Ar_1$ is phenylene or pyridinediyl;
$Ar_2$ is phenylene or fluorophenylene;
L is selected from the group consisting of —SO$_2$NH—, —NHSO$_2$—, —C(=O)NH—, —NHC(=O)—, and —NHC(=O)NH—;
Z is selected from the group consisting of (CH$_2$)$_n$COOH,

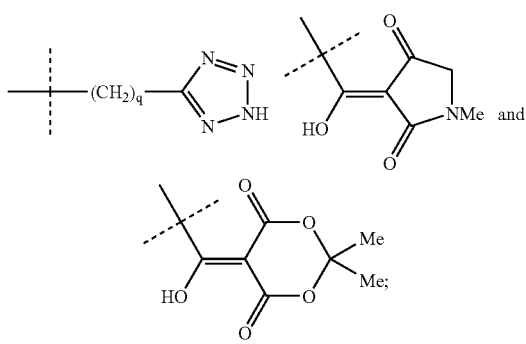

n is 0 or 1; and
q is 0 are preferred.

The compound of formula I which is 4-(4-acetyl-3-hydroxy-2-propyl-phenoxy methyl)-N-[2-(2H-tetrazol-5-yl)-phenyl]-benzenesulfonamide is more preferred.

Further embodiments of the invention include a process for preparing the compound of formula I, or a pharmaceutically acceptable salt thereof, comprising the steps selected from (A) for a compound of formula I where Z is tetrazolyl,

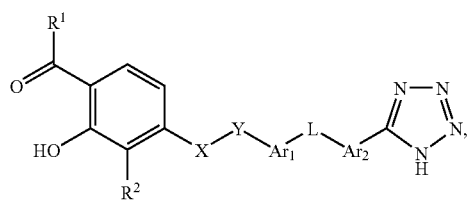

Z is tetrazolyl cycloaddition of a compound of formula II where $R^{10}$ is cyano with an azide reagent,

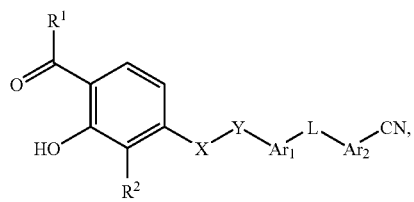

$R^{10}$ is cyano (B) for a compound of formula I where Z is COOH,

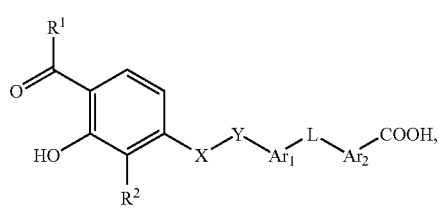

Z is COOH hydrolysis of a compound of formula II wherein $R^{10}$ is $COOR^{14}$ and $R^{14}$ is selected from the group consisting of C1-C5 alkyl, phenyl and benzyl;

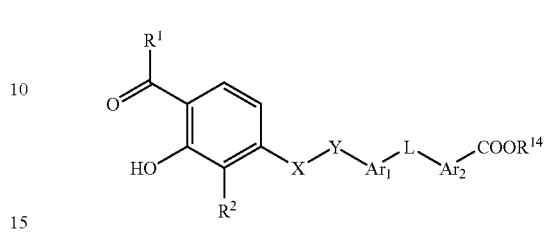

and
(C) for a compound of formula I where Z is COOH,

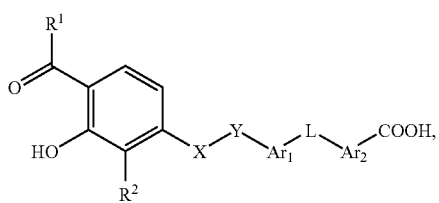

Z is COOH hydrolysis of a compound of formula II where $R^{10}$ is cyano;

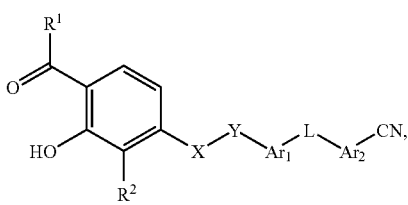

$R^{10}$ is cyano whereafter, when a pharmaceutically acceptable salt of the compound of formula I is required, it is obtained by reacting the acid of formula I with a physiologically acceptable base or by reacting a basic compound of formula I with a physiologically acceptable acid or by any other conventional procedure.

A further embodiment of the present invention provides intermediate compounds useful for the preparation of a compound of formula I. More specifically, the present invention provides a compound of formula II

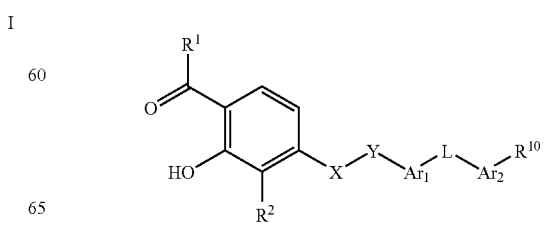

wherein

R$^1$, R$^2$, X, Y, Ar$_1$, Ar$_2$ and L are defined as above;

R$^{10}$ is CN or COOR$^{14}$ in which R$^{14}$ is selected from the group consisting of C1-C5 alkyl, phenyl and benzyl. A particular value of R$^{14}$ is methyl.

Compounds of the present invention may be made by a process which is analogous to one known in the chemical art for the production of structurally analogous compounds or by a novel process described herein. Such processes useful for the manufacture of a compound of formula I as defined above are provided as further features of the invention and are illustrated by the following procedures in which, unless otherwise specified, the meanings of the generic radicals are as defined above and all reagents are well known and appreciated in the art.

Generally, a compound of formula I may be prepared from a compound of formula II where R$^{10}$ represents a precursor to Z (Reaction Scheme A, step a). More specifically, a compound of formula II where R$^{10}$ is COOCH$_3$ or cyano is reacted with a suitable base such as potassium hydroxide in a suitable solvent such as water to provide a compound of formula I where Z is carboxylic acid. Additionally, a compound of formula II where R$^{10}$ is cyano is reacted with an azide reagent to provide a compound of formula I where Z is tetrazolyl. Azide reagents include HN$_3$ wherein HN$_3$ is provided by reaction of sodium azide and an acid. Suitable acids include the protic acids such as triethylamine hydrochloride and ammonium chloride. Other examples of azide reagents include the trialkylsilylazides such as trimethylsilylazide or a transition metal azide complex as provided by zinc bromide and sodium azide. A compound of formula II where R$^{10}$ is an acid halide is reacted in one or more steps with cyclocondensating agents to provide a compound of formula I where Z is

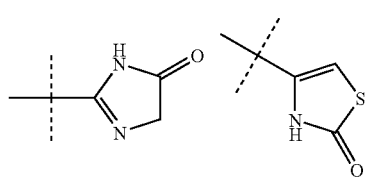

-continued

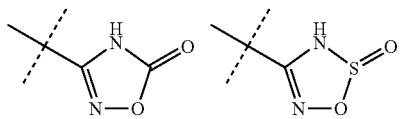

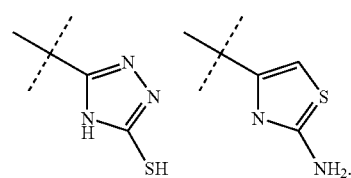

A compound of formula of II may be prepared from a compound of formula III (Reaction Scheme A, step b) or, alternatively, from a compound of formula V (Reaction Scheme A, step c). More specifically in step b, a compound of formula III where X is O is reacted under Mitsunobu conditions with a compound of formula IV where R$^{11}$ is OH in the presence of an organophosphine such as tributylphosphine and an appropriate azodicarbonyl reagent such as 1,1'-(azodicarbonyl)dipiperidine to provide a compound of formula II. Suitable solvents include toluene and dichloromethane. In step b, a compound of formula II may also be prepared by reacting a compound of formula III where X is O, S, NH with a compound of formula IV where R$^{11}$ is a leaving group in the presence of a suitable base such as cesium carbonate and a suitable solvent such as acetone. Suitable leaving groups include halides such as iodide, and sulfonate esters such as methanesulfonate ester.

Reaction Scheme A

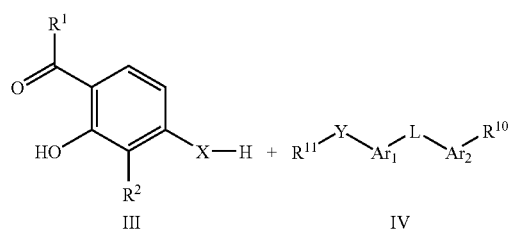

III           IV

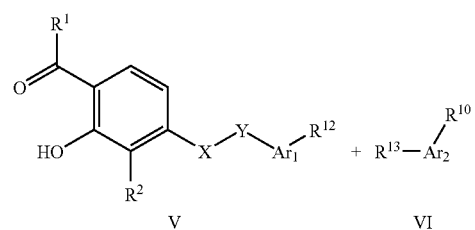

V           VI step b            step c

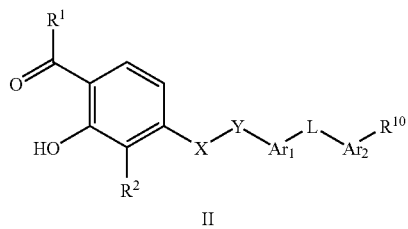

II

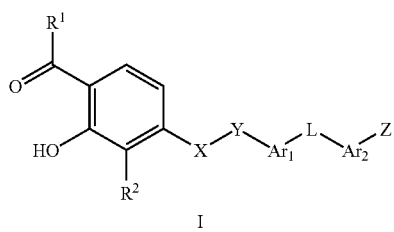

I

Alternatively, a compound of formula of II may be prepared from a compound of formula V (Reaction Scheme A, step c) where $R^{12}$ is an appropriate precursor to the group L. More specifically, a compound of formula V where $R^{12}$ is amino is reacted with a compound of formula VI where $R^{13}$ is acyl chloride in the presence of a suitable base in a solvent such as dichloromethane to provide a compound of formula II where L is amido. Suitable bases include a tertiary amine such as triethylamine. Analogously, a compound of formula V where $R^{12}$ is amino is reacted with a compound of formula VI where $R^{13}$ is sulphonyl chloride in the presence of a suitable base in a solvent to provide a compound of formula II where L is sulphonamido. In addition, a compound of formula V where $R^{12}$ is amino is reacted with a compound of formula VI where $R^{13}$ is isocyanato in a solvent such as dichloromethane to provide a compound of formula II where L is ureido.

A compound of formula III where $R^2$ is halo, phenyl, substituted phenyl, thiophenyl, substituted thiophenyl and the like maybe prepared from a compound of formula VII (Reaction Scheme B). More specifically, a compound of formula VII where X is O is reacted under the appropriate halogenation conditions to provide a compound of formula III where X is O and $R^2$ is a halogen such as chloro, bromo or iodo. A compound of formula III where X is O and $R^2$ is a halogen such as chloro, bromo or iodo is reacted with a boronic acid of phenyl, substituted phenyl, thiophenyl, substituted thiophenyl and the like in the presence of a transition metal catalyst such as $Pd(dppf)_2Cl_2$ and a base such as cesium hydroxide to provide a compound of formula III where $R^2$ is the corresponding phenyl, substituted phenyl, thiophenyl, substituted thiophenyl and the like. The reaction is conveniently carried out in a solvent such as solutions of tetrahydrofuran and water.

Reaction Scheme B

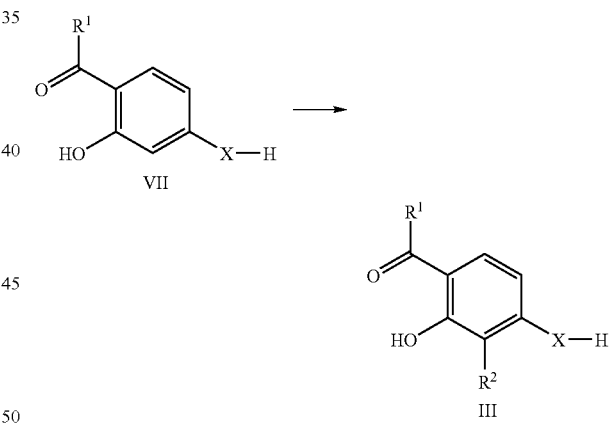

A compound of formula III where X is S may be prepared from a compound of formula III where X is O. More specifically, a compound of formula III where X is O is reacted with dimethylthiocarbamoyl chloride in a suitable solvent such as dichloromethane. The resulting thiocarbamate is heated in a suitable solvent such as dodecane and treated with sodium hydroxide to provide a compound of formula III where X is S.

A compound of formula III may also be prepared from a compound of formula IX where the group Pg represents a suitable protecting group (Reaction Scheme C). More specifically in step a, a compound of formula IX where $R^2$ is a halogen such iodo or bromo and Pg is methyl, is reacted with a boronic acid of phenyl, substituted phenyl, thiophenyl, substituted thiophenyl and the like in the presence of a transition metal catalyst such as $Pd(dppf)_2Cl_2$ and a base such as cesium hydroxide to provide a compound of formula IX where $R^2$ is phenyl, substituted phenyl, thiophenyl, substituted thiophenyl and the like, and Pg is methyl. The reaction is conveniently carried out in a solvent such as a solution of tetrahydrofuran and water. Further in step a, a compound of formula IX where $R^2$ is phenyl, substituted phenyl, thiophenyl, substituted thiophenyl and the like is reacted with an $R^1$ acyl halide such as acetyl chloride and a Lewis acid such as aluminum chloride in a suitable solvent to provide a compound of formula VIII where $R^1$ is methyl and $R^2$ is phenyl, substituted phenyl, thiophenyl, substituted thiophenyl and the like. Suitable solvents include dichloromethane. In step b, a compound of formula VIII where the group Pg is methyl is reacted with deprotection agents such as pyridine hydrochloride in the presence of microwave radiation to provide a compound of formula III where $R^2$ is phenyl, substituted phenyl, thiophenyl, substituted thiophenyl and the like.

O, and Pg is benzyl. In step b, a compound of formula VIII where $R^1$ is methyl, $R^2$ is trifluoromethyl, X is O, and Pg is benzyl is reacted with a transition metal catalyst such as palladium hydroxide in the presence of an effective hydrogen source such as cyclohexene to provide a compound of formula III where $R^1$ is methyl, $R^2$ is trifluoromethyl, and X is O. Suitable solvents include ethanol.

A compound of formula IV where L is C(=O)NH may be prepared from a compound of formula XI as outlined in Reaction Scheme D. More specifically in step a, a compound of formula XI where $R^{11}$ is a leaving group including a halogen such as chloro is reacted with a compound of formula XII and a base such as potassium carbonate to provide a compound of formula IVa where L is C(=O)NH. Analogously, a compound of formula XIa is reacted with a compound of formula XII in the presence of a base in a solvent to provide a compound of formula IVb where L is $SO_2NH$.

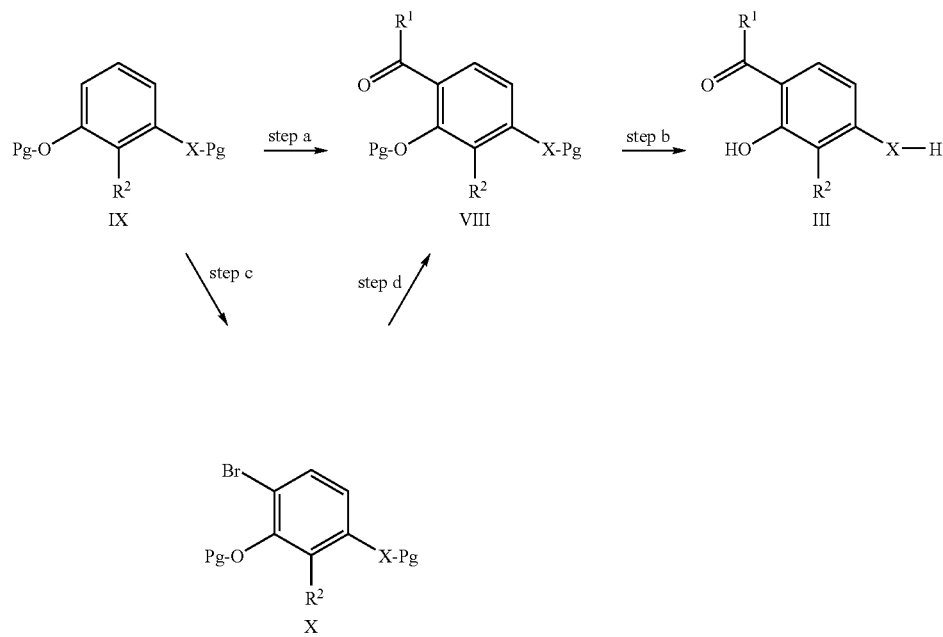

Additionally in Reaction Scheme C, a compound of formula III where $R^2$ is C1-C3 fluoroalkyl may be prepared from a compound of formula IX where $R^2$ is a halogen. More specifically, a compound of formula IX where $R^2$ is iodo, X is O and Pg is a suitable protecting group such as benzyl is reacted with an alkyl ester of difluoro-fluorosulfonyl-acetic acid in the presence of hexamethylphosphoramide and a transition metal catalyst such as copper iodide in a suitable solvent to provide a compound of formula IX where $R^2$ is trifluoromethyl, X is O, and Pg is benzyl. Suitable solvents include dimethylformamide. In step c, a compound of formula IX where $R^2$ is trifluoromethyl, X is O, and Pg is benzyl is reacted N-bromosuccinimide in a suitable solvent such as dimethylformamide to provide a compound of formula X. In step d, a compound of formula X is reacted with tributyl-(1-ethoxy-vinyl)-stannane and a transition metal catalyst such as tetrakis(triphenylphosphine)palladium in a solvent such as dioxane followed by acid hydrolysis to provide a compound of formula VIII where $R^1$ is methyl, $R^2$ is trifluoromethyl, X is

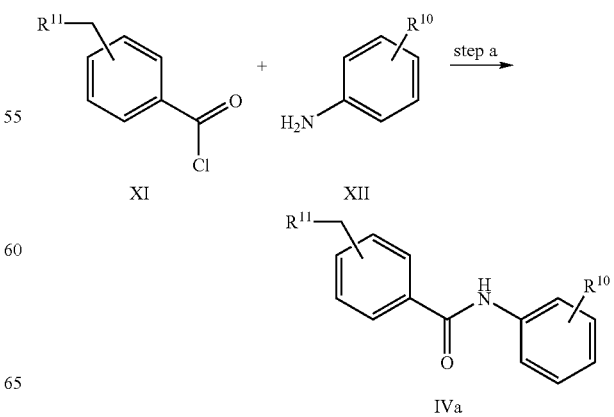

-continued

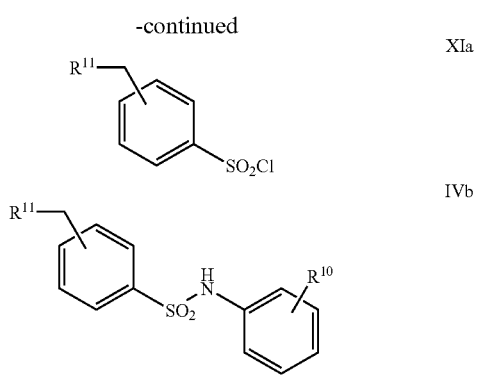

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience of crystallization, increased solubility, and the like.

In practice, the compounds of formula I are usually administered in the form of pharmaceutical compositions, that is, in admixture with pharmaceutically acceptable carriers or diluents, the proportion and nature of which are determined by the chemical properties of the selected compound of formula I, the chosen route of administration, and standard pharmaceutical practice.

Thus, the present invention provides pharmaceutical compositions comprising a compound of the formula I and a pharmaceutically acceptable carrier, diluent or excipient.

The compounds of formula I can be administered by a variety of routes. In effecting treatment of a patient afflicted with disorders described above, a compound of formula I can be administered in any form or mode which makes the compound bioavailable in an effective amount, including oral and parenteral routes. For example, compounds of formula I can be administered orally, by inhalation, subcutaneously, intramuscularly, intravenously, transdermally, intranasally, rectally, ocularly, topically, sublingually, buccally, and the like. Oral administration is generally preferred for treatment of the neurological and psychiatric disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions of the present invention are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. A person skilled in the art may determine preferred compositions and preparations according to the present invention.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of formula I present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the formula I or its pharmaceutical salt from about 0.1 to about 10% w/v (weight per unit volume).

The compounds of formula I are potentiators of metabotropic glutamate (mGlu) receptor function, in particular they are potentiators of mGlu2 receptors. That is the compounds of formula I increase mGlu2 receptor response to glutamate or a glutamate agonist, enhancing the function of the receptors. The behavior of the potentiators of formula I at mGlu2 receptors is shown in Example A which is suitable to identify potentiators useful for carrying out the present invention. Thus, the potentiators of the present invention are expected to be useful in the treatment of various neurological and psychiatric disorders associated with glutamate dysfunction described to be treated herein and others that can be treated by such potentiators as are appreciated by those skilled in the art.

Example A

Potentiation of Glutamate-Induced Increase in Intracellular Calcium with a mGlu2 Expressing Cell Line Cell lines expressing human mGlu2 receptors are derived as previously described (Desai, Burnett, Mayne, Schoepp, *Mol. Pharmacol.* 48, 648-657, 1995) and cultured in DMEM with 5% dialyzed fetal bovine serum, 1 mM glutamine, 1 mM sodium pyruvate, 50 μg/mL Geneticin G418, and 0.2 mg/mL hygromycin B. Confluent cultures are passaged weekly. These cells are referred to as RGT cells for Rat Glutamate Transporter, and have been co-transfected with the glutamate/ aspartate transporter GLAST. The RGT cell line expressing the mGlu2 receptors is stably transfected with the promiscuous G-protein, Galpha15 to change the signaling pathway to the mGlu2 receptor to one that could be easily measured through release of intracellular calcium. Thus, intracellular calcium levels are monitored before and after the addition of drugs on a Fluorometric Imaging Plate Reader (i.e. FLIPR, Molecular Devices). The following buffer is used throughout as an assay buffer: 10 mM KCl, 138 mM NaCl, 5 mM Ca Cl$_2$, 1 mM MgCl$_2$, 4 mM Na H$_2$PO$_4$, 10 mM Glucose, 10 mM HEPES, pH 7.4. Cells that had been plated 48 hours prior at a density of 30-40,000 cells per well in a 96-well plate are loaded with a calcium-sensitive dye for 90 minutes at 25° C. Fluo-3 (2 mM in DMSO, Molecular Probes) are mixed with a equal volume of 10% pluronic acid in DMSO, and diluted to 8 μM into the buffer described above containing 10% fetal bovine serum to make the loading buffer. Following loading of the cells, the loading buffer is removed and replaced with assay buffer prior to drug addition and monitoring on the FLIPR. The resulting signal from the addition of compounds of formula (I) and submaximal concentrations of a glutamate-site agonist (e.g. 1 μM glutamate) is determined by taking the difference of the maximal fluorescent peak height minus the background fluorescence in each well and expressing the results as a percent of the signal seen with a maximal glutamate response (30 μM glutamate, typically about 30-50,000 Relative Fluorescent Units). Least squares curve fitting with a four-parameter equation is then applied to the resulting dose-% response curve to determine the resulting EC$_{50}$ values.

Exemplified compounds of formula (I) affect the potentiation of mGlu2 receptors at EC$_{50}$ values less than 12.5 μM. More specifically, examples 1, 3, 8, 10, 12, 13 and 17 affect the potentiation of mGlu2 receptors at EC$_{50}$ values less than 100 mM.

Compounds of formula I are modulators of leukotriene receptor function, in particular they are antagonists of leukotriene receptors. That is the compounds of formula I antagonize the cysteinyl-leukotriene D4 (LTD4) receptor. The behavior of the antagonism of the cysteinyl-leukotriene D4 (LTD4) receptor by compounds of formula I is shown in Example B which is suitable to identify antagonists useful for carrying out the present invention. Thus, the leukotriene antagonists of the present invention are useful in the treatment of various inflammatory and allergic disorders mediated by leukotrienes and described to be treated herein and other disorders that can be treated by such antagonists as are appreciated by those skilled in the art.

Example B

Antagonism of Cysteinyl-leukotriene D4 (LTD4)—Induced Increase in Intracellular Calcium within a Cysteinyl-Leukotriene 1 (CysLT1) Receptor Expressing Cell Line Cell lines expressing the human CysLT1 receptor [AV12-664 (ATCC-9595)] are derived and maintained in culture media: DMEM with 5% dialyzed fetal bovine serum, 1 mM glutamine, and 1 mM sodium pyruvate. Confluent cultures are passaged weekly. Intracellular calcium levels are monitored in the CysLT1-expressing cells with the addition of LTD4, with or without prior exposure to the compounds being tested as antagonists with a Fluorometric Imaging Plate Reader (FLIPR, Molecular Devices). The following buffer is used throughout as an assay buffer: Hanks Buffered Saline Solution without phenol red (GIBCO), with 10 mM HEPES pH 7.4. Cells that had been plated 48 hours prior at a density of 20-25,000 cells per well in a 96-well plate are loaded with a calcium-sensitive dye for 90 minutes at 25° C. Fluo-3 (2 mM in DMSO, Molecular Probes) is mixed with an equal volume of 10% pluronic acid in DMSO, and diluted to 8 μM in the buffer described above containing 10% fetal bovine serum to make the loading buffer. Following loading of the cells, the buffer is removed and replaced with assay buffer prior to drug addition and monitoring on the FLIPR for several minutes. The resulting signal from the addition of 6 nM LTD4 (provides approximately 90% of the maximal signal with 25 nM LTD4) is determined by taking the difference of the maximal fluorescent peak height minus the background fluorescence in each well and expressing the results as a percent of the signal seen without pretreatment of the test compound(s). Least squares curve fitting with a four-parameter equation is applied to the resulting dose-% inhibition curve to determine the resulting IC$_{50}$ values.

Exemplified compounds of formula (I) affect the antagonism of CysLT1 receptors at IC$_{50}$ values less than 12.5 μM. More specifically, examples 1, 8, 10, 12, 13 and 17 affect the antagonism of CysLT1 receptors at IC$_{50}$ values less than 500 nM.

In one embodiment of the present invention provides methods of treating neurological and psychiatric disorders associated with glutamate dysfunction, comprising administering to a patient in need thereof an effective amount of a potentiator of metabotropic glutamate 2 receptors.

Specifically, the present invention provides a method of treating neurological and psychiatric disorders associated with glutamate dysfunction, comprising administering to a patient in need thereof an effective amount of a potentiator of the mGlu2 receptor and/or antagonist of the CysLT1 receptor, that is, the present invention provides methods using an effective amount of a potentiator of mGlu2 receptors and/or antagonist of the CysLT1 receptor.

In a preferred embodiment the present invention provides a method for treating migraine, comprising administering to a patient in need thereof an effective amount of a compound of formula I.

In another preferred embodiment the present invention provides a method for treating asthma, comprising administering to a patient in need thereof an effective amount of a compound of formula I.

In another preferred embodiment the present invention provides a method for treating anxiety, comprising administering to a patient in need thereof an effective amount of a compound of formula I.

Particularly preferred anxiety disorders are generalized anxiety disorder, panic disorder, and obsessive compulsive disorder.

In another preferred embodiment the present invention provides a method for treating schizophrenia, comprising administering to a patient in need thereof an effective amount of a compound of formula I.

In yet another preferred embodiment the present invention provides a method for treating epilepsy, comprising administering to a patient in need thereof an effective amount of a compound of formula I.

Because the compounds of formula I enhance the normal physiological function of the mGlu receptors, the compounds of formula I are useful for the treatment of a variety of neurological and psychiatric disorders associated with glutamate dysfunction, including: acute neurological and psychiatric disorders such as cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, multiple sclerosis, ocular damage, retinopathy, cognitive disorders, idiopathic and drug-induced Parkinson's disease, muscular spasms and disorders associated with muscular spasticity (including tremors) seizures, epilepsy, convulsions, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic pain states, severe pain, intractable pain, neuropathic pain, and post-traumatic pain), tardive dyskinesia, sleep disorders (including narcolepsy), attention deficit/hyperactivity disorder, and conduct disorder.

At present, the fourth edition of the Diagnostic and Statistical Manual of Mental Disorders (DSM-IV™) (1994, American Psychiatric Association, Washington, D.C.), provides a diagnostic tool for identifying many of the disorders described herein. The skilled artisan will recognize that there are alternative nomenclatures, nosologies, and classification systems for neurological and psychiatric disorders described herein and that these systems evolve with medical scientific progress.

The compounds of formula I potentiate mGlu receptor response, in particular mGlu2 receptor response, to glutamate and glutamate agonists. Such agonists are easily recognized and some are available in the art. Schoepp, D. D., Jane, D. E., Monn, J. A., *Neuropharmacology* 38: 1431-1476, (1999).

Thus, a more particular embodiment, it is understood that the present invention extends to a method of potentiating the action of a glutamate receptor agonist at the Group II mGlu receptors, comprising administering to a patient in need thereof an effective amount of a mGlu2 potentiator, in particular a compound of formula I, in combination with a potentiated amount of an mGlu receptor agonist. Such a combination may be advantageous in that it may augment the activity and selectivity of mGlu agonist.

As used herein, the term "patient" refers to a warm blooded animal such as a mammal which is afflicted with one or more neurological and psychiatric disorders associated with glutamate dysfunction. It is understood that guinea pigs, dogs, cats, rats, mice, horses, cattle, sheep, and humans, and particularly humans, are examples of animals within the scope of the meaning of the term. It is also understood that this invention relates specifically to the potentiation of mammalian metabotropic glutamate receptors.

It is also recognized that one skilled in the art may affect the neurological and psychiatric disorders by treating a patient presently afflicted with the disorders or by prophylactically treating a patient afflicted with the disorders with an effective amount of the compound of formula I. Thus, the terms "treatment" and "treating" are intended to refer to all processes wherein there may be a slowing, interrupting, arresting, controlling, or stopping of the progression of the neurological and psychiatric disorders described herein, but does not necessarily indicate a total elimination of all disorder symptoms, and is intended to include prophylactic treatment of such neurological and psychiatric disorders.

As used herein, the term "effective amount" of a compound of formula I refers to an amount, that is, the dosage which is effective in treating the neurological and psychiatric disorders described herein.

The attending diagnostician, as one skilled in the art, can readily determine an effective amount by the use of conventional techniques and by observing results obtained under analogous circumstances. In determining an effective amount, the dose of a compound of formula I, a number of factors are considered by the attending diagnostician, including, but not limited to: the compound of formula I to be administered; the co-administration of an mGlu agonist, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of formula I is expected to vary from about 0.01 milligram per kilogram of body weight per day (mg/kg/day) to about 100 mg/kg/day. Preferred amounts may be determined by one skilled in the art.

As used herein, the term "potentiated amount" refers to an amount of an mGlu agonist, that is, the dosage of agonist which is effective in treating the neurological and psychiatric disorders described herein when administered in combination with an effective amount of a compound of formula I. A potentiated amount is expected to be less than the amount that is required to provided the same effect when the mGlu agonist is administered without an effective amount of a compound of formula I.

The attending diagnostician, as one skilled in the art, can readily determine a potentiated amount by the use of conventional techniques and by observing results obtained under analogous circumstances. In determining a potentiated amount, the dose of an mGlu agonist to be administered in combination with a compound of formula I, a number of factors are considered by the attending diagnostician, including, but not limited to: the mGlu agonist selected to be administered, including its potency and selectivity; the compound of formula I to be co-administered; the species of mammal; its size, age, and general health; the specific disorder involved; the degree of involvement or the severity of the disorder; the response of the individual patient; the modes of administration; the bioavailability characteristics of the preparations administered; the dose regimens selected; the use of other concomitant medication; and other relevant circumstances.

A potentiated amount of an mGlu agonist to be administered in combination with an effective amount of a compound of formula I is expected to vary from about 0.1 milligram per kilogram of body weight per day (mg/kg/day) to about 100 mg/kg/day and is expected to be less than the amount that is required to provided the same effect when administered without an effective amount of a compound of formula I. Preferred amounts of a co-administered mGlu agonist are able to be determined by one skilled in the art.

Of the neurological and psychiatric disorders associated with glutamate dysfunction which are treated according to the present invention, the treatment of migraine, anxiety, schizophrenia, and epilepsy are particularly preferred. Particularly preferred anxiety disorders are generalized anxiety disorder, panic disorder, and obsessive compulsive disorder.

Thus, in a preferred embodiment the present invention provides a method for treating migraine, comprising administering to a patient in need thereof an effective amount of a compound of formula I or a pharmaceutical composition thereof.

In one of the available sources of diagnostic tools, *Dorland's Medical Dictionary* (23$^{rd}$ Ed., 1982, W.B. Saunders Company, Philidelphia, Pa.), migraine is defined as a symptom complex of periodic headaches, usually temporal and unilateral, often with irritability, nausea, vomiting, constipation or diarrhea, and photophobia. As used herein the term "migraine" includes these periodic headaches, both temporal and unilateral, the associated irritability, nausea, vomiting, constipation or diarrhea, photophobia, and other associated symptoms. The skilled artisan will recognize that there are alternative nomenclatures, nosologies, and classification systems for neurological and psychiatric disorders, including migraine, and that these systems evolve with medical scientific progress.

In another preferred embodiment the present invention provides a method for treating anxiety, comprising administering to a patient in need thereof an effective amount of a compound of formula I or a pharmaceutical composition thereof.

At present, the fourth edition of the Diagnostic and Statistical Manual of Mental Disorders (DSM-IV™) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

A number of preclinical laboratory animal models for migraine and anxiety have been described. One commonly used model of migraine is the dural extravasation model that has been described by Phebus et al., Life Sci., 61(21), 2117-2126 (1997) which can be used to evaluate the present compounds.

Example C

Animal Model of Dural Plasma Protein Extravasation (PPE)

Male Harlan Sprague-Dawley rats (250-350 g) are anesthetized with sodium pentobarbital (65 mg/kg, i.p.) and placed in a stereotaxic frame (David Kopf Instruments) with the incisor bar set at −2.5 mm. Following a midline sagital scalp incision, two pairs of bilateral holes are drilled through the skull (3.2 mm posterially, 1.8 and 3.8 mm laterally, all coordinates referenced to bregma). Pairs of stainless steel stimulating electrodes, insulated except at the tips (Rhodes Medical Systems, Inc.), are lowered through the holes in both hemispheres to a depth of 9.2 mm.

The femoral vein is exposed and a dose of the test compound is injected intravenously (i.v.) at a dosing volume of 1 mL/kg Approximately 8 minutes post i.v. injection, a 20 mg/kg dose of Fluorescein isothiocyanate-bovine serum albumin (FITC-BSA) is also injected intravenously. The FITC-BSA functions as a marker for protein extravasation. Exactly 10 minutes post-injection of the test compound, the left trigeminal ganglion is stimulated for 5 minutes at a current intensity of 1.0 mA (5 Hz, 5 msec duration) with a Model S48 Grass Instrument Stimulator with PSIU6 photoelectric isolation unit (Grass-Telefactor).

Alternatively, rats fasted overnight are dosed orally with test compound via gavage at a volume of 2 mL/kg. Approximately 50 minutes later the animals are anesthetized and placed in the stereotaxic frame as described above. Exactly 58 minutes post-p.o. dosing, the animals are dosed with FITC-BSA (20 mg/kg, i.v.). Exactly one hour post-p.o. dosing, the animals are stimulated as described above.

Five minutes following stimulation, the animals are killed by exsanguination with 40 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monochromator and a spectrophotometer is used to quantify the amount of FITC-BSA in each sample. An excitation wavelength of approximately 490 nm is utilized and the emission intensity at 535 nm was determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion is an ipsilateral effect (i.e. occurs only on the side of the dura in which the trigeminal ganglion was stimulated). This allows the use of the other (unstimulated) half of the dura as a control. The ratio of the amount of extravasation in the dura from the stimulated side, over the amount of extravasation in the unstimulated side, is calculated. Control animals dosed only with saline, yield a ratio of approximately 2.0. In contrast, a compound which effectively prevented the extravasation in the dura from the stimulated side would yield a ratio of approximately 1.0.

The fear potentiated startle response model has been extensively used as a model of anxiety and can be used to evaluate the present compounds. Davis, *Psychopharmacol.*, 62, 1 (1979); Davis, *Behav. Neurosci.*, 100, 814 (1986); Davis, *Tr. Pharmacol. Sci.*, 13, 35 (1992).

Example D

Fear Potentiated Startle Paradigm

Male Sprague-Dawley rats weighing 325-400 g are purchased from Harlan Sprague-Dawley, Inc. (Cumberland, Ind.) and given a one week acclimation period before testing. Rats are individually housed with food and water ad libitum in an animal room on a 12-hour light/dark cycle with lights on between 6:00 A.M. and 6:00 P.M. The test compound of formula I is prepared in a suspension of 5% ethanol, 0.5% CMC, 0.5% Tween 80 and 99% water. 2S-2-amino-2-(1S,2S-2-carboxycyclopropan-1-yl)-3-(xanth-9-yl)propionic acid is prepared in sterile water. Control rats are given the respective vehicle.

The fear potentiated startle paradigm is conducted over three consecutive days. All three days begin with a 5-minute adaptation period before the trial starts. On day one (baseline startle) after the adaptation period, the animal receives 30 trials of 120 dB auditory noise. The mean startle amplitude ($V_{max}$) is used to assign animals to groups with similar means before conditioning begins. Day two consists of conditioning the animals. Each animal receives 0.5 mA of shock for 500 msec preceded by a 5 second presentation of light which remains on for the duration of the shock. Ten presentations of the light and shock are administered. Day three is the testing trial where drug administration occurs prior to testing. Twenty-four hours after conditioning, startle testing sessions are conducted. Ten trials of acoustic startle (120 dB), non-light paired, are presented at the beginning of the session. This is followed by 20 random trials of the noise alone and 20 random trials of noise preceded by light. Excluding the first 10 trials, the startle response amplitudes for each trial type are averaged for each animal. Data is presented as the difference between light+noise and noise-alone. Differences in startle response amplitudes are analyzed by JMP statistical software using a One-way Anova (analysis of variance, t-test). Group differences are considered to be significant at $p<0.05$.

In another preferred embodiment the present invention provides a method for treating epilepsy, comprising administering to a patient in need thereof an effective amount of a compound of formula I or a pharmaceutical composition thereof.

At present, there are several types and subtypes of seizures associated with epilepsy, including idiopathic, symptomatic, and cryptogenic. These epileptic seizures can be focal (partial) or generalized. They can also be simple or complex. Epilepsy is described in the art, such as Epilepsy: A comprehensive textbook. Ed. by Jerome Engel, Jr. and Timothy A. Pedley. (Lippincott-Raven, Philadelphia, 1997). At present, the International Classification of Diseases, Ninth Revision, (ICD-9) provides a diagnostic tool including epilepsy and related disorders. These include: generalized nonconvulsive epilepsy, generalized convulsive epilepsy, petit mal status epilepticus, grand mal status epilepticus, partial epilepsy with impairment of consciousness, partial epilepsy without impairment of consciousness, infantile spasms, epilepsy partialis continua, other forms of epilepsy, epilepsy, unspecified, NOS. As used herein the term "epilepsy" includes these all types and subtypes. The skilled artisan will recognize that there are alternative nomenclatures, nosologies, and classification systems for neurological and psychiatric disorders, including epilepsy, and that these systems evolve with medical scientific progress.

Various electroshock-induces models has been extensively used as a model of seizure disorders.

Example E

Electroshock-Induced Seizures

Application of electrical stimulation by corneal electrodes to mice can induce tonic hindlimb-extensor seizures. Blockade of tonic extensor seizures induced by electroshock is considered predictive for drugs which block seizure propagation and may be effective in preventing various seizures in humans, including epileptic seizures.

Vehicle or a dose of a test drug are administered to groups of 5 to 10 mice each. Thirty minutes later, electroshock (10 mA, 0.2 sec duration) is administered by transcorneal electrodes. The number of mice exhibiting tonic extensor seizures in each group is recorded. The data are reported as the percentage of mice that are protected from seizures.

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "N" refers to normal or normality; "M" refers to molar or molarity; "mol" refers to mole or moles; "mmol" refers to millimole or millimoles; "mmol" refers to micromole or micromoles; "kg" refers to kilogram or kilograms; "g" refers to gram or grams; "mg" refers to microgram or micrograms; "mg" refers to milligram or milligrams; "mL" refers to microliter or microliters; "mL" refers milliliter or milliliters; "L" refers to liter or liters; "bp" refers to boiling point; "mp" refers to melting point; "brine" refers to a saturated aqueous sodium chloride solution; "h or hr" refers to hour or hours; "min" refers to minute or minutes; "MS" refers to mass spectrometry; "NMR" refers to nuclear magnetic resonance spectroscopy; "TFA" refers to trifluoroacetic acid; "$CH_2$—$Cl_2$" or "DCM" refers to dichloromethane; "DCE" refers to dichloroethane; "MeOH" refers to methanol; "$NH_4OH$" refers to a concentrated aqueous ammonia solution; "HCl" refers to hydrogen chloride; "MTBE" refers to tert-butyl methyl ether; "DSC" refers to differential scanning calorimetery. "DMEM" refers to Dulbecco's modified eagle medium. Chemical shifts are give in δ and NMR spectra were obtained in $CDCl_3$, unless otherwise indicated.

Preparation 1

Synthesis of 2-iodo-benzene-1,3-diol

Add sodium bicarbonate (27.9 g, 333 mmol) to a solution of benzene-1,3-diol (33.0 g, 300 mmol), and iodine (81.5 g, 321 mmol) in water (225 mL) chilled to 0° C. and stir. Warm the solution to ambient temperature gradually over 1 hour. Extract with diethyl ether, combine organic layers, dry with sodium sulfate, filter and concentrate under reduced pressure to yield a white solid. Triturate the solid in chloroform (100 mL) chilled to −10° C. After 30 minutes, filter the precipitate, washing with cold chloroform to yield the title compound as a white solid (49.0 g, 69%): $^1$H NMR (DMSO-$d_6$) δ 6.33 (d, 2H), 6.93 (t, 1H), 10.03 (s, 2H).

Preparation 2

Synthesis of 1,3-bis-benzyloxy-2-iodo-benzene

Add benzyl bromide (7.97 g, 46.6 mmol) to a solution of 2-iodo-benzene-1,3-diol (5.00 g, 21.2 mmol) and cesium carbonate (15.2 g, 46.6 mmol) in dimethylformamide (200 mL) and stir. After 18 hours, concentrate under reduced pressure. Add water (500 mL) and stir. After 1 hour, filter the resulting precipitate washing with water and hexanes to yield the title compound as an off-white solid (6.30 g, 71%): $^1$H NMR (CDCl$_3$) δ 5.18 (s, 4H), 6.55 (d, 2H), 7.19 (t, 1H), 7.29-7.53 (m, 10H).

Preparation 3

Synthesis of 1,3-bis-benzyloxy-2-trifluoromethyl-benzene

Add difluoro-fluorosulfonyl-acetic acid methyl ester (15.0 g, 78.1 mmol) to a solution of 1,3-bis-benzyloxy-2-iodo-benzene (6.50 g, 15.6 mmol), hexamethylphosphoramide (13.99 g, 78.1 mmol), and copper iodide (3.57 g, 18.7 mmol) in dimethylformamide (50 mL) and stir. Heat reaction to 80° C. After 18 hours, cool to ambient temperature. Add saturated aqueous ammonium chloride (250 mL) and extract with ether. Combine organic layers, and wash with saturated aqueous sodium bicarbonate, brine, dry with magnesium sulfate, filter and concentrate under reduced pressure to give a residue. Purify the residue by flash chromatography eluting with 20% ethyl acetate:hexanes to yield the title compound as a clear oil (4.60 g, 82%): $^1$H NMR (CDCl$_3$) δ 5.14 (s, 4H), 6.67 (d, 2H), 7.29-7.46 (in, 11H).

Preparation 4

Synthesis of 1,3-bis-benzyloxy-4-bromo-2-trifluoromethyl-benzene

Add N-bromosuccinimide (4.67 g, 26.23 mmol) to a solution of 1,3-bis-benzyloxy-2-trifluoromethyl-benzene (9.40 g, 26.2 mmol) in dimethylformamide (100 mL) and stir. After 18 hours add water and extract with diethyl ether. Combine organic layers, dry with sodium sulfate, filter and concentrate under reduced pressure to yield the title compound as an orange oil (11.20 g, 98%): $^1$H NMR (CD$_3$CN) δ 4.97 (2, 2H), 5.18 (s, 2H), 6.99 (d, 1H), 7.33-7.55 (m, 10H), 7.79 (d, 1H).

Preparation 5

Synthesis of 1-(2,4-bis-benzyloxy-3-trifluoromethyl-phenyl)-ethanone

Add tetrakis(triphenylphosphine)palladium (2.93 g, 2.54 mmol) to a solution of 1,3-bis-benzyloxy-4-bromo-2-trifluoromethyl-benzene (11.10 g, 25.4 mmol) and tributyl-(1-ethoxy-vinyl)-stannane (10.08 g, 27.92 mmol) in dioxane (250 mL) and stir. Purge reaction vessel with argon. Heat to 100° C. After 6 hours, cool to ambient temperature and concentrate under reduced pressure. Add 2N aqueous hydrochloric acid (50 mL), and tetrahydrofuran (200 mL) and stir. After 30 minutes add water and extract with ethyl acetate. Combine organic layers, dry with sodium sulfate, filter and concentrate under reduced pressure to yield a residue. Purify the residue by flash chromatography eluting with a gradient of 0-20% ethyl acetate:hexanes to yield the title compound as a clear oil (6.10 g, 60%): $^1$H NMR (CD$_3$CN) δ 2.48 (s, 3H), 4.89 (s, 2H), 5.25 (s, 2H), 7.08 (d, 1H), 7.33-7.48 (m, 10H), 7.83 (d, 1H).

Preparation 6

Synthesis of 1-(2,4-dihydroxy-3-trifluoromethyl-phenyl)-ethanone

Add 20% palladium hydroxide on carbon (11.0 g, 15 mmol) to a solution of 1-(2,4-bis-benzyloxy-3-trifluoromethyl-phenyl)-ethanone (6.00 g, 15 mmol) in ethanol (75 mL) and cyclohexene (75 mL) and stir. Purge the reaction vessel with argon. Heat to reflux. After 18 hours, cool to ambient temperature, filter and concentrate under reduced pressure to yield the title compound as a grey solid (3.00 g, 91%): $^1$H NMR (CD$_3$CN) δ 2.55 (s, 3H), 6.51 (d, 1H), 7.88 (d, 1H), 13.91 (bs, 1H).

Preparation 7

Synthesis of dimethyl-thiocarbamic acid S-(4-acetyl-3-hydroxy-2-propyl-phenyl)ester Stir a mixture of 1-(2,4-dihydroxy-3-propyl-phenyl)-ethanone (2 g, 10.3 mmol), triethylamine (1.6 mL 11.3 mmol), and dichloromethane (40 mL) at room temperature. Add dimethylthiocarbamoyl chloride (1.27 g, 10.3 mmol) and stir at room temperature overnight. Wash the mixture with 1M hydrochloric acid (25 mL), dry over magnesium sulfate, filter and concentrate. Purify the residue via silica chromatography eluting with hexanes to 7:3 hexanes:ethyl acetate to afford dimethyl-thiocarbamic acid O-(4-acetyl-3-hydroxy-2-propyl-phenyl) ester (1.2 g, 41%) as a light yellow solid. Stir the yellow solid in tetradecane (10 mL) at 250° C. for an hour and purify by silica chromatography eluting with hexanes to 6:4 hexanes:ethyl acetate to give the title compound (1.08 g, 90%) as a white solid. LCMS (m/z) 280 m−1.

Preparation 8

Synthesis of 1-(2-hydroxy-4-mercapto-3-propyl-phenyl)-ethanone

Reflux a stirred mixture of dimethyl-thiocarbamic acid S-(4-acetyl-3-hydroxy-2-propyl-phenyl)ester (1.08 g, 3.84 mmol), potassium hydroxide (1.1 g, 19.2 mmol), ethanol (25 mL), and water (10 mL) for 2 hours. Cool the reaction in an ice/water bath and adjust the pH to 2 with aqueous 5N hydrochloric acid. Extract the mixture with ethyl acetate (3×50 mL). Combine the extracts and wash with water (50 mL) and brine (50 mL) and dry over magnesium sulfate, filter, and concentrate to afford the title compound (0.76 g, 94%) as a brown oil which solidifies on standing. LCMS (m/z) 211 m−1.

Preparation 9

Synthesis of 2-fluoro-3-methoxy-phenol

A mixture of 2-fluoroanisole (1.8 ml, 15.85 mmol), pentamethyldiethyenetriamine (3.6 mL, 17.45 mmol) and tetrahydrofuran (10 mL) is stirred at −78° C. A 2.5 M solution of n-butyllithium in hexanes (7 ml, 17.45 mmol) is added dropwise and the resulting solution is stirred at −78° C. 2 hr. Trimethylborate (2 mL, 17.45 mmol) is added and the reaction is warmed to room temperature and stirred 1 hr. Acetic acid (1.4 ml, 23.8 mmol) is added followed by an aqueous 30% solution of hydrogen peroxide (1.8 mL, 17.45 mmol) and the resulting mixture is stirred rapidly 18 hr at room temperature. The reaction mixture is diluted with water and extracted with ethyl acetate (3×50 mL). The combined extracts are dried over magnesium sulfate, filtered and concentrated to about 10 mL volume. The resulting mixture is purified via silica chromatography eluting with hexanes to 8:1 hexanes:ethyl acetate to give the title compound (1.65 g, 73%) as a colorless oil. MS ES 141 m−1.

Preparation 10

Synthesis of 1-(3-fluoro-2,4-dihydroxy-phenyl)-ethanone

A solution of 2-fluoro-3-methoxy-phenol (0.5 g, 3.53 mmol) and dichloromethane is stirred at −78° C. A 1M solution of boron tribromide in dichloromethane (3.9 mL, 3.9 mmol) is added slowly and the mixture is stirred 10 min cold, then warmed to 0° C. and stirred 1 hr. The reaction is quenched with ice and stirred at room temperature overnight. The product is extracted with ethyl acetate (2×50 mL), dried over magnesium sulfate, filtered, and concentrated. The resulting residue is combined with boron trifluoride diethyl etherate (1.3 mL, 10.3 mmol) and acetic acid (0.2 mL, 3.28 mmol) and heated to reflux 8 hr. The mixture is cooled to room temperature, diluted with water (50 mL), and extracted with ethyl acetate (3×50 mL). The combined extracts are dried over magnesium sulfate, filtered and concentrated to about 10 mL volume. The resulting mixture is diluted with hexanes (50 mL), cooled to 0° C., and filtered to give the title compound (310 mg, 58%) as a tan solid. MS ES 171 m+1.

Preparation 11

Synthesis of 1-(3-chloro-2,4-dihydroxy-phenyl)-ethanone

A solution of 2,4,-dihydroxyacetophenone (6 g, 39.4 mmol), aqueous 1M sodium hydroxide (41.4 mL, 41.4 mmol) and water (200 mL) is stirred at room temperature. An aqueous 1.6M solution of sodium hypochlorite (32 mL) is added over a 1 hr period. The resulting dark brown solution is stirred 18 hr at room temperature. The reaction mixture is adjusted to a pH of 2-3 with concentrated aqueous hydrochloric acid. The resulting suspension is filtered and washed with water (4×100 mL). The filtered solid was dried under vacuum at 45° C. for 2.5 days to give the title compound (4.8 g, 65%) as a brown solid. LCMS 1 187 m+.

Preparation 12

Synthesis of 1-(3-chloro-2,4-dihydroxy-phenyl)-propan-1-one

The title compound is prepared in a similar manner to 1-(3-chloro-2,4-dihydroxy-phenyl)-ethanone (Preparation 11) employing 2,4-dihydroxypropiophenone to give 4.5 g, 37% of an off-white solid. LCMS 1 201 m+.

Preparation 13

Synthesis of 1-[2-hydroxy-4-(4-nitro-benzyloxy)-3-propyl-phenyl]-ethanone

To 2',4'-dihydroxy-3'-propyl acetophenone (3.0 g, 15.4 mmol) and 4-nitrobenzyl bromide (3.6 g, 17 mmol) in acetone (62 mL) is added K₂CO₃ (3.2 g, 23 mmol). The reaction mixture is refluxed for 1 h and cooled to room temperature. The precipitate is filtered, washed with water (5×70 mL), and dried to give the title compound (4.8 g, 94%). LC-MS (m/z): 328 (M−1).

Preparation 14

Synthesis of 1-[4-(4-amino-benzyloxy)-2-hydroxy-3-propyl-phenyl]-ethanone

To 1-[2-hydroxy-4-(4-nitro-benzyloxy)-3-propyl-phenyl]-ethanone (1.0 g, 3.0 mmol) in tetrahydrofuran (13 mL) is added concentrated hydrochloric acid (2.7 mL) and stannous chloride dihydrate (2.2 g, 9.9 mmol). The reaction mixture is stirred at room temperature overnight. The reaction mixture is quenched into saturated aqueous NH₄Cl (100 mL). The resulting emulsion is filtered and the filtrate extracted with ethyl acetate (3×100 mL). The combined organic layers are washed with brine, dried over sodium sulfatesodium sulfate, and concentrated to provide the title compound in crude form (980 mg,). LC-MS (m/z): 298 (M−1).

Preparation 15

Synthesis of 3-{3-[4-(4-acetyl-3-hydroxy-2-propyl-phenoxymethyl)-phenyl]-ureido}-benzoic acid ethyl ester To 1-[4-(4-amino-benzyloxy)-2-hydroxy-3-propyl-phenyl]-ethanone (980 mg, 30% pure by LC-MS) in anhydrous CH₂Cl₂ (4 mL) is added ethyl 3-isocyanatobenzoate (0.18 mL) at room temperature under Ar gas. The reaction mixture is stirred at room temperature overnight. The resulting white precipitate is filtered to give the title compound (215 mg). LC-MS (m/e): 491 (M+1).

Example 1

Synthesis of 3-{3-[4-(4-acetyl-3-hydroxy-2-propyl-phenoxymethyl)-phenyl]-ureido}-benzoic acid

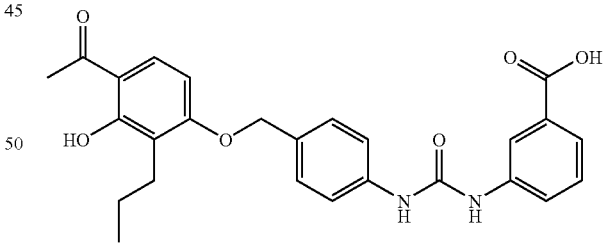

To 3-{3-[4-(4-acetyl-3-hydroxy-2-propyl-phenoxymethyl)-phenyl]-ureido}-benzoic acid ethyl ester (200 mg, 0.40 mmol) in 1:1 tetrahydrofuran:methanol (10 mL) is added 2 N NaOH (5 mL). The reaction mixture is stirred vigorously at room temperature for 3 h. The reaction mixture is diluted with water (30 mL), acidified with 5N hydrochloric acid to pH=4, and extracted with ethyl acetate (3×70 mL). The combined organic extracts are washed with brine, dried over sodium sulfate, and concentrated to dryness. The resulting residue is purified by reverse phase HPLC using a gradient of 90:10 to 20:80 (H₂O/0.1% TFA):CH₃CN as eluent to give the title compound (24 mg, 12%). LC-MS (m/e): 461 (M−1); ¹H NMR (DMSO-$d_6$) δ 12.93 (1H, s), 12.85 (1 H, s), 8.93 (1 H, s), 8.77 (1 H, s), 8.15 (1H, s), 7.82 (1H, s), 7.30-7.60 (7 H, m), 6.75 (1H, d), 5.20 (2 H, s), 2.60 (5 H, m), 1.50 (2 H, m), 0.90 (3 H, t).

Preparation 16

Synthesis of 1-(2,6-dihydroxy-biphenyl-3-yl)-ethanone

To a solution of 1-(2,4-dihydroxy-3-iodo-phenyl)-ethanone (1.0 g, 3.59 mmol; 581938, may be prepared as described in G. Batu and R. Stevenson, *J. Org. Chem.* 1979, 44, 3948) in tetrahydrofuran/water (15 mL/3 mL) at room temperature is added phenyl boronic acid (0.877 g, 7.19 mmol), Pd(dppf)$_2$Cl$_2$ (0.088 g, 0.107 mmol), and cesium hydroxide monohydrate (1.81 g, 10.8 mmol). After stirring for 15 hours, the mixture is filtered through a pad of filter cel, washing with ethyl acetate. The residue is diluted with 30 mL of 1N hydrochloric acid and extracted with ethyl acetate. The combined organic phases are washed with brine; dried over magnesium sulfate; filtered and concentrated under reduced pressure. The resulting residue is purified by flash chromatography, eluting with 30% ethyl acetate/hexanes to give the title compound as a colorless solid: MS (m/z) 228(M+); $^1$H NMR (DMSO-$d_6$) δ 13.1 (s, 1H), 10.6 (bs, 1H), 7.81 (d, J=8.8 Hz, 1H), 7.41-7.28 (m, 5H), 6.61 (d, J=8.8 Hz, 1H), 2.58 (s, 3H); $R_f$=0.58 in 40% ethyl acetate/hexanes.

Preparation 17

Synthesis of 1-(4'-fluoro-2,6-dihydroxy-biphenyl-3-yl)-ethanone

The title compound is prepared essentially as described in Preparation 16 using 4-fluorophenylboronic acid: mass spectrum (n/e): 245(M−1); $^1$H NMR (acetone-$d_6$) δ 13.2 (s, 1H), 7.82 (d, J=8.4 Hz, 1H), 7.44-7.40 (m, 2H), 7.18-7.13 (m, 2H), 6.61 (d J=8.8 Hz, 1H), 2.60 (s, 3H); $R_f$=0.40 in 40% ethyl acetate/hexanes.

Preparation 18

Synthesis of 4-fluoro-3-nitro-benzoic acid methyl ester

Heat a solution of 4-fluoro-3-nitro-benzoic acid (5.00 g, 27.0 mmol, Sigma Chemical Co.) in methanol (135 mL, 0.2M) at reflux and slowly add oxalyl chloride (6.86 g, 54.0 mmol, Aldrich Chemical Co.) through reflux condenser. Stir for 2 h at reflux. Concentrate reaction mixture in vacuo. The title compound solidifies upon standing (5.30 g, 26.6 mmol, 99%): $^{19}$F NMR (acetone-$d_6$, 400 MHz) δ-121.3.

Preparation 19

Synthesis of 3-amino-4-fluoro-benzoic acid methyl ester

Stir mixture of 4-fluoro-3-nitro-benzoic acid methyl ester (5.30 g, 26.6 mmol) and palladium (5% on carbon, 5.66 g, 2.66 mmol, Aldrich Chemical Co.) in ethanol (0.2 M). Carefully introduce hydrogen (balloon) and stir the reaction for 24 h. Filter the reaction mixture through a glass-fiber filter and wash the filter cake with ethanol. Concentrate the filtrate to afford the title compound (4.00 g, 23.6 mmol, 89%): MS (m/z): 170 (M+1).

Preparation 20

Synthesis of 4-chloromethyl-N-(4-cyano-phenyl)-benzamide

Add 4-aminobenzonitrile (3.125 g, 26.4 mmol) and potassium carbonate (8.04 g, 58.2 mmol) to a solution of 4-chloromethyl-benzoyl chloride (5.00 g, 26.4 mmol) in acetone (60 mL). Heat at reflux for 4 hours. Cool to room temperature, filter, and concentrate to afford the title compound as a yellow solid (7.30 g, 91%): $^1$H NMR (DMSO-$d_6$) δ 4.86 (s, 2H), 7.61 (d, 2H), 7.83 (d, 2H), 7.94-8.03 (m, 4H), 10.72 (s, 1H).

The following compounds are prepared essentially by the method of Preparation 20.

| Prep. No. | Chemical name | Structure | Physical data |
|---|---|---|---|
| 21 | 3-Chloro methyl-N-(3-cyano-phenyl)-benzamide | 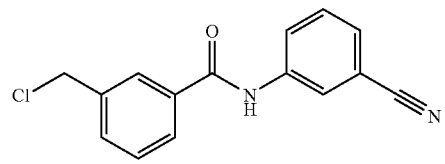 | $^1$H NMR (DMSO-$d_6$) δ 4.87 (s, 2 H), 7.56-7.60 (m, 3 H), 7.70 (d, 1 H), 7.95 (d, 1 H), 8.02 (s, 1 H), 8.05 (m, 1 H), 8.25 (s, 1 H), 10.63 (s, 1 H). |
| 22 | 3-(4-Chloro methyl-benzoyl amino)-benzoic acid methyl ester | 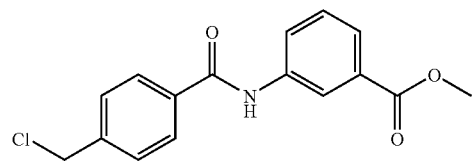 | $^1$H NMR (CDCl$_3$) δ 3.92 (s, 3 H), 4.64 (s, 2 H), 7.46 (t, 1 H), 7.52 (d, 2 H), 7.83 (d, 1 H), 7.87 (d, 2 H), 7.97 (bs, 1 H), 8.05 (d, 1 H), 8.15 (s, 1 H). |

-continued

| Prep. No. | Chemical name | Structure | Physical data |
|---|---|---|---|
| 23 | 4-(3-Chloro methyl-benzoyl amino)-benzoic acid methyl ester | 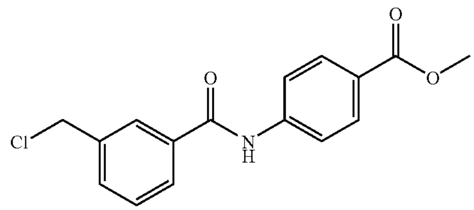 | $^1$H NMR (CDCl$_3$) δ 3.92 (s, 3 H), 4.66 (s, 2 H), 7.51 (t, 1 H), 7.61 (d, 1 H), 7.75 (d, 2 H), 7.82 (d, 1 H), 7.90 (s, 1 H), 7.96 (bs, 1 H), 8.07 (d, 2 H). |
| 24 | 4-(4-Chloro methyl-benzoyl amino)-benzoic acid methyl ester | 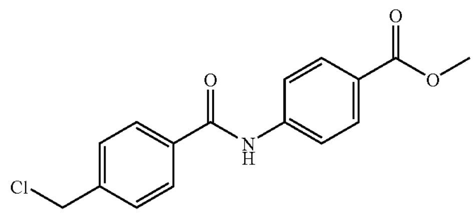 | $^1$H NMR (CDCl$_3$) δ 3.92 (s, 3 H), 4.64 (s, 2 H), 7.53 (d, 2 H), 7.74 (d, 2 H), 7.87 (d, 2 H), 7.93 (bs, 1 H), 8.07 (d, 2 H). |
| 25 | 3-(3-Chloro methyl-benzoyl amino)-4-fluoro-benzoic acid methyl ester | 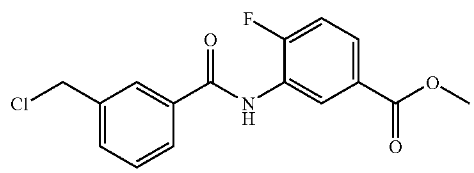 | $^{19}$F NMR (acetone-d$_6$, 400 MHz) δ −113.2. |
| 26 | 3-(4-Chloro methyl-benzoyl amino)-4-fluoro-benzoic acid methyl ester | 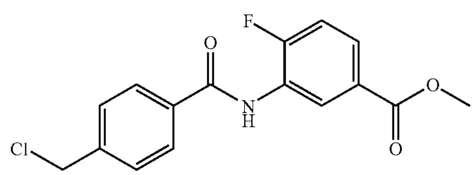 | $^{19}$F NMR (acetone-d$_6$, 400 MHz) δ −113.3. |
| 27 | [4-(3-Chloromethyl-benzoylamino)-phenyl]-acetic acid ethyl ester | 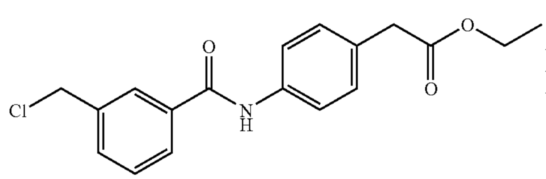 | $^1$H NMR (CDCl$_3$) δ 1.26 (t, 3 H), 3.60 (s, 2 H), 4.15 (q, 2 H), 4.64 (s, 2 H), 7.28 (d, 2 H), 7.48 (t, 1 H), 7.57 (d, 1 H), 7.59 (d, 2 H), 7.80 (d, 1 H), 7.86 (bs, 1 H), 7.88 (s, 1 H). |

Preparation 28

Synthesis of 4-(4-acetyl-3-hydroxy-2-propyl-phenoxymethyl)-N-(4-cyano-phenyl)-benzamide Add 4-chloromethyl-N-(4-cyano-phenyl)-benzamide (1.00 g, 3.69 mmol) to a solution of 1-(2,4-dihydroxy-3-propyl-phenyl)-ethanone (717 mg, 3.69 mmol) in dimethylformamide (14 mL). After 10 minutes add potassium carbonate (766 mg, 5.54 mmol) and cesium carbonate (1.204 g, 3.69 mmol). Stir at room temperature for one hour, then heat to 70° C. for 1.5 hours. Cool, and partition between ethyl acetate (100 mL) and water (100 mL). The organic phase is washed twice with water, brine, dried, and concentrated to dryness. The resulting residue is purified by silica gel column chromatography, eluting with 1:1 hexane:ethyl acetate to afford the title compound (820 mg, 52%): $^1$H NMR (CDCl$_3$) δ 0.97 (t, 3H), 1.58 (m, 2H), 2.56 (s, 3H), 2.73 (m, 2H), 5.25 (s, 2H), 6.46 (d, 1H), 7.56-7.60 (m, 3H), 7.68 (d, 2H), 7.79 (d, 2H), 7.88-7.94 (m, 3H), 12.77 (s, 1H).

The following compounds are prepared essentially by the method of Preparation 28.

| Prep. No. | Chemical name | Structure | Physical data |
|---|---|---|---|
| 29 | 3-(4-Acetyl-3-hydroxy-2-propyl-phenoxy-methyl)-N-(3-cyano-phenyl)-benzamide | 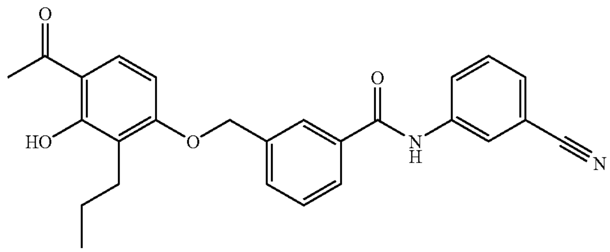 | $^1$H NMR (DMSO-d$_6$) δ 0.88 (t, 3 H), 1.50 (m, 2 H), 2.58 (s, 3 H), 2.60 (m, 2 H), 5.37 (s, 2 H), 6.75 (d, 1 H), 7.58-7.63 (m, 3 H), 7.69 (d, 1 H), 7.82 (d, 1 H), 7.94 (d, 1 H), 8.03-8.06 (m, 2 H), 8.25 (s, 1 H), 12.85 (s, 1 H). |
| 30 | 3-[3-(4-Acetyl-3-hydroxy-2-propyl-phenoxy methyl)-benzoylamino]-benzoic acid methyl ester | 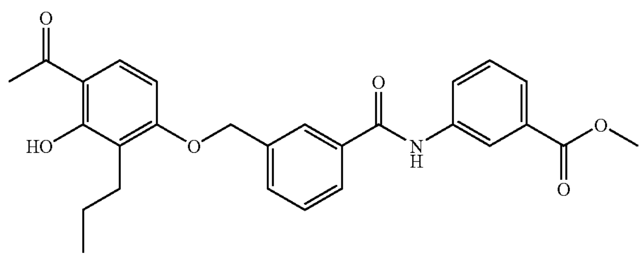 | $^1$H NMR (CDCl$_3$) δ 0.97 (t, 3 H), 1.60 (sextet, 2 H), 2.66 (s, 3 H), 2.72 (t, 2 H), 3.92 (s, 3 H), 5.22 (s, 2 H), 6.47 (d, 1 H), 7.47 (t, 1 H), 7.54 (t, 1 H), 7.58 (d, 1 H), 7.63 (d, 1 H), 7.82-7.85 (m, 2 H), 7.95 (s, 1 H), 8.00 (s, 1 H), 8.05 (d, 1 H), 8.15 (s, 1 H), 12.75 (s, 1 H); MS (APCI-neg mode) m/z (rel intensity) 460 (100). |
| 31 | 4-[3-(4-Acetyl-3-hydroxy-2-propyl-phenoxy-methyl)-benzoyl amino]-benzoic acid methyl ester | 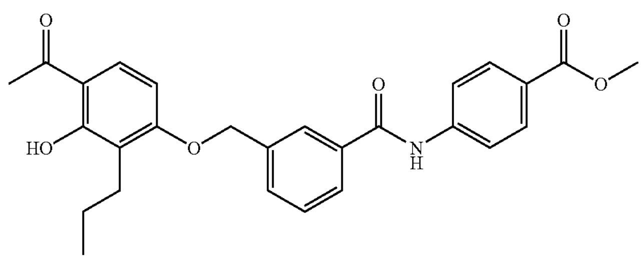 | $^1$H NMR (CDCl$_3$) δ 0.96 (t, 3 H), 1.60 (sextet, 2 H), 2.56 (s, 3 H), 2.72 (t, 2 H), 3.91 (s, 3 H), 5.24 (s, 2 H), 6.48 (d, 1 H), 7.55 (t, 1 H), 7.59 (d, 1 H), 7.64 (d, 1 H), 7.74 (d, 2 H), 7.82 (d, 1 H), 7.94 (s, 1 H), 8.07 (d, 2 H), 12.75 (s, 1 H); MS (APCI-neg mode) m/z (rel intensity) 460 (100). |
| 32 | 4-[4-(4-Acetyl-3-hydroxy-2-propyl-phenoxy methyl)-benzoyl-amino]-benzoic acid methyl ester | 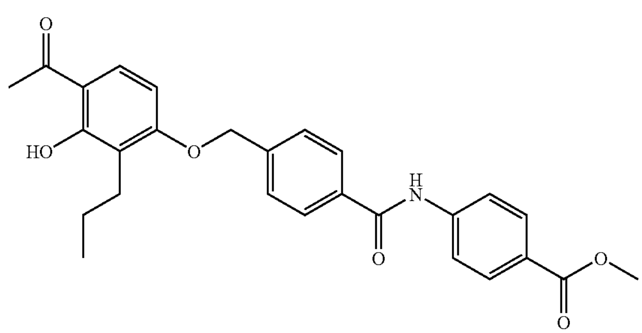 | $^1$H NMR (CDCl$_3$) δ 0.97 (t, 3 H), 1.59 (sextet, 2 H), 2.57 (s, 3 H), 2.72 (t, 2 H), 3.92 (s, 3 H), 5.24 (s, 2 H), 6.45 (d, 1 H), 7.53-7.60 (m, 3 H), 7.75 (d, 2 H), 7.91 (d, 2 H), 7.99 (bs, 1 H), 8.07 (d, 2 H). |
| 33 | 3-[3-(4-Acetyl-3-hydroxy-2-propyl-phenoxy methyl)-benzoyl amino]-4-fluoro benzoic acid methyl ester | 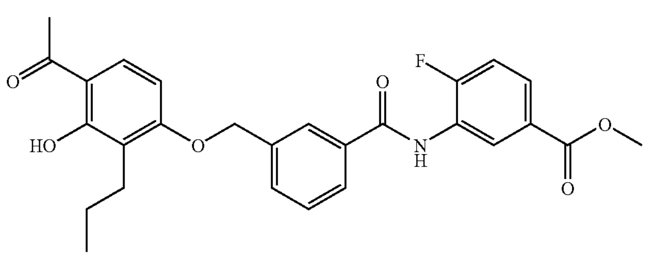 | MS (m/z): 478 (M − 1). |

-continued

| Prep. No. | Chemical name | Structure | Physical data |
|---|---|---|---|
| 34 | 3-[4-(4-Acetyl-3-hydroxy-2-propyl-phenoxymethyl)-benzoyl amino]-4-fluoro benzoic acid methyl ester | 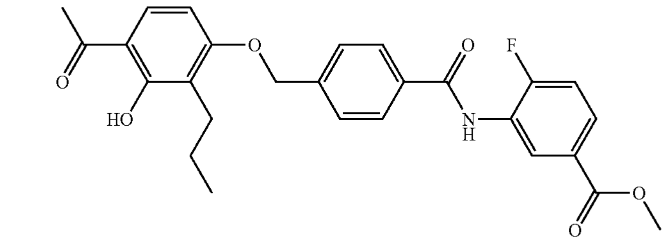 | MS (m/z): 478 (M − 1). |
| 35 | {4-[3-(4-Acetyl-3-hydroxy-2-propyl-phenoxymethyl)-benzoylamino]-phenyl}-acetic acid ethyl ester | 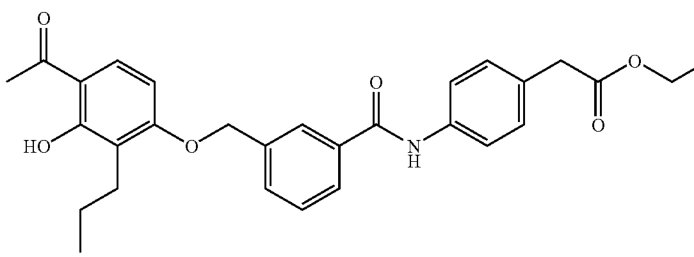 | $^1$H NMR (CDCl$_3$) δ 0.97 (t, 3 H), 1.26 (t, 3 H), 1.60 (sextet, 2 H), 2.56 (s, 3 H), 2.72 (t, 2 H), 3.60 (s, 2 H), 4.15 (q, 2 H), 5.23 (s, 2 H), 6.48 (d, 1 H), 7.30 (d, 2 H), 7.48-7.64 (m, 6 H), 7.80-7.83 (m, 2 H), 7.93 (s, 1 H), 12.75 (s, 1 H). |

Example 2

Synthesis of 3-(4-acetyl-3-hydroxy-2-propyl-phenoxymethyl)-N-[3-(2H-tetrazol-5-yl)-phenyl]-benzamide

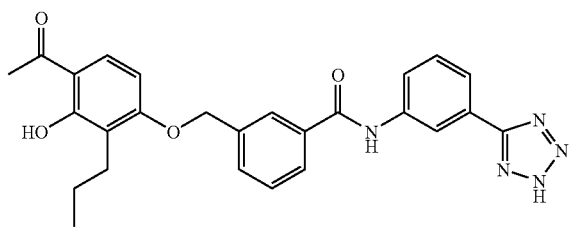

Heat a mixture of 3-(4-acetyl-3-hydroxy-2-propyl-phenoxymethyl)-N-(3-cyano-phenyl)-benzamide, sodium azide (1.12 g, 17.3 mmol), and ammonium chloride in dimethylformamide at 110 C for 24 hours. Cool to room temperature and dilute with water. Filter and wash several times with water. Dry filtered material and dissolve in hot acetone. Purify the resulting solution via chromatography, eluting with hexanes:acetone with 1% acetic acid to afford the title compound. $^1$H NMR (DMSO-d$_6$) δ 0.88 (t, 3H), 1.52 (sextet, 2H), 2.58 (s, 3H), 2.62 (t, 2H), 5.37 (s, 2H), 6.76 (d, 1H), 7.57 (d, 1H), 7.61 (d, 1H), 7.68 (d, 1H), 7.74 (d, 1H), 7.82 (d, 1H), 7.97 (m, 2H), 8.09 (m, 1H), 8.59 (s, 1H), 10.56 (s, 1H), 12.85 (s, 1H); MS (APCI-neg mode) m/z (rel intensity) 470 (100).

Example 3

Synthesis of 3-[3-(4-acetyl-3-hydroxy-2-propyl-phenoxymethyl)-benzoylamino]-benzoic acid

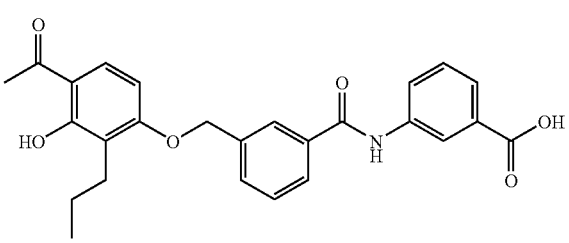

Add 1N lithium hydroxide (30 mL) to a solution of 3-[3-(4-acetyl-3-hydroxy-2-propyl-phenoxymethyl)-benzoylamino]-benzoic acid methyl ester (4.00 g, 8.67 mmol) in tetrahydrofuran (40 mL). Stir overnight at room temperature and then dilute with water. Acidify the resulting mixture (the salt precipitated) with 1N hydrochloric acid. Concentrate to remove the organic solvents, filter and wash with water several times, then with hexanes. Dry to afford the title compound as a white powder (3.56 g, 92%): $^1$H NMR (DMSO-d$_6$) δ 0.83 (t, 3H), 1.50 (sextet, 2H), 2.58 (s, 3H), 2.62 (t, 2H), 5.36 (s, 2H), 6.75 (d, 1H), 7.49 (t, 1H), 7.59 (t, 1H), 7.67 (d, 1H), 7.71 (d, 1H), 7.82 (d, 1H), 7.96 (d, 1H), 8.04 (d, 1H), 8.06 (s, 1H), 8.41 (s, 1H), 10.49 (s, 1H), 12.85 (s, 1H), 13.00 (bs, 1H); MS (APCI-neg mode) m/z (rel intensity) 446 (100).

The following compounds are prepared essentially by the method of Example 3.

| Ex. # | Chemical name | Structure | Physical data |
|---|---|---|---|
| 4 | 4-[3-(4-Acetyl-3-hydroxy-2-propyl-phenoxymethyl)-benzoylamino]-benzoic acid | 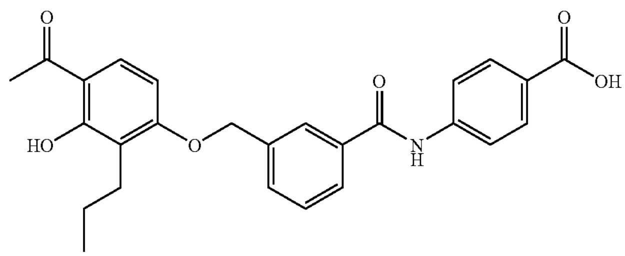 | ¹H NMR (DMSO-d₆) δ 0.88 (t, 3 H), 1.51 (sextet, 2 H), 2.58 (s, 3 H), 2.60 (t, 2 H), 5.36 (s, 2 H), 6.75 (d, 1 H), 7.60 (t, 1 H), 7.67 (d, 1 H), 7.82 (d, 1 H), 7.94 (s, 4 H), 7.95 (d, 1 H), 8.07 (s, 1 H), 10.63 (s, 1 H), 12.76 (bs, 1 H), 12.85 (s, 1 H); MS (APCI-neg mode) m/z (rel intensity) 446 (100). |
| 5 | 3-[3-(4-Acetyl-3-hydroxy-2-propyl-phenoxy methyl)-benzoyl amino]-4-fluoro-benzoic acid | 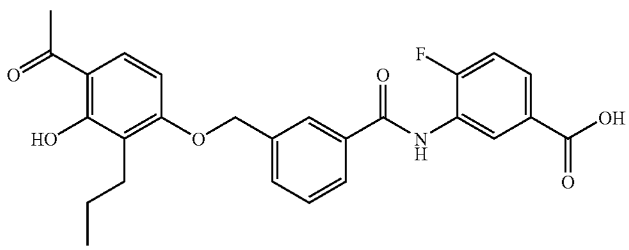 | ¹H NMR (400 MHz, acetone-d₆) δ 0.93 (t, J = 7.2 Hz, 3 H), 1.60 (m, 2 H), 2.59 (s, 3 H), 2.71 (t, J = 7.6 Hz, 2 H), 5.39 (s, 2 H), 6.76 (d, J =9.0 Hz, 1 H), 7.40 (m, 1 H), 7.62 (m, 1 H), 7.76 (d, J = 6.6 Hz, 1 H), 7.81 (d, J = 9.0 Hz, 1 H), 8.03 (d, J = 8.2 Hz, 1 H), 8.19 (s, 1 H), 8.80 (m, 1 H), 12.9 (s, 1 H). MS (m/z): 464 (M − 1). |
| 6 | 3-[4-(4-Acetyl-3-hydroxy-2-propyl-phenoxy methyl)-benzoyl amino]-4-fluoro-benzoic acid | 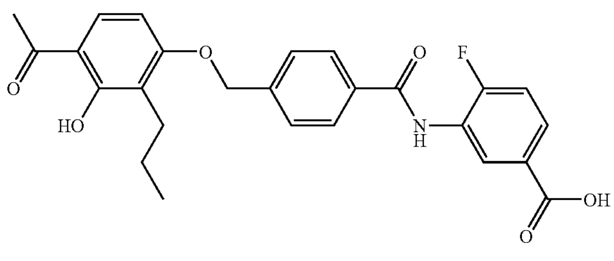 | ¹H NMR (400 MHz, acetone-d₆) δ 0.95 (t, J = 7.4 Hz, 3 H), 1.59 (m, 2 H), 2.59 (s, 3 H), 2.72 (t, J = 7.6 Hz, 2 H), 5.39 (s, 2 H), 6.79 (d, J = 7.8 Hz, 1 H), 7.42 (m, 1 H), 7.68 (d, J = 7.8 Hz, 2 H), 7.85 (d, J = 7.8 Hz, 1 H), 7.95 (m, 1 H), 8.10 (d, J = 7.8 Hz, 2 H), 8.81 (m, 1 H), 9.39 (s, 1 H), 12.91 (s, 1 H). MS (m/z): 464 (M − 1). |
| 7 | {4-[3-(4-Acetyl-3-hydroxy-2-propyl-phenoxy methyl)-benzoylamino]-phenyl}-acetic acid | 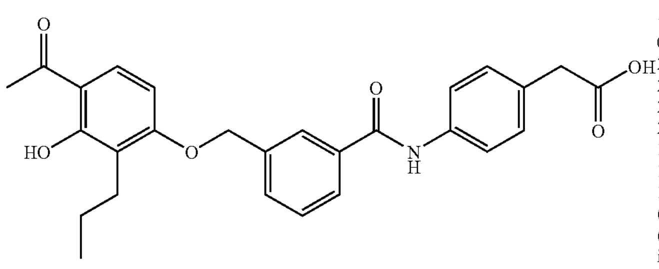 | ¹H NMR (DMSO-d₆) δ 0.88 (t, 3 H), 1.52 (sextet, 2 H), 2.58 (s, 3 H), 2.62 (t, 2 H), 3.54 (s, 2 H), 5.36 (s, 2 H), 6.75 (d, 1 H), 7.24 (d, 2 H), 7.57 (t, 1 H), 7.65 (d, 1 H), 7.70 (d, 2 H), 7.82 (d, 1 H), 7.92 (d, 1 H), 8.04 (s, 1 H), 10.28 (s, 1 H), 12.30 (bs, 1 H), 12.85 (s, 1 H); MS (APCI-neg mode) m/z (rel intensity) 460 (100). |

Preparation 36

Synthesis of 4-bromomethyl-N-(3-cyano-phenyl)-benzenesulfonamide

Add 4-bromomethyl-sulfonyl chloride (4.00 g, 14.8 mmol) to a solution of 3-aminobenzonitrile (1.70 g, 14.1 mmol) and pyridine (1.23 g, 15.51 mmol) in dichloromethane (70 mL) at 0° C. After 3 hours at 0° C., pour solution into 1N hydrochloric acid (100 mL) and extract with dichloromethane (100 mL), dry the organic phase with sodium sulfate, filter and concentrate under reduced pressure. Purify by flash chromatography to yield the title compound as a white solid (3.727 g, 10.6 mmol): MS (m/z): 349 (M−1).

The following compounds are prepared essentially by the method of Preparation 36.

| Prep. No. | Chemical name | Structure | Physical data |
|---|---|---|---|
| 37 | 4-Bromo methyl-N-(4-cyano-phenyl)-benzenesulfonamide | 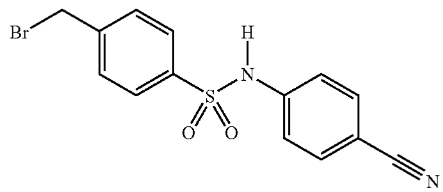 | MS (m/z): 349 (M − 1). |
| 38 | 4-Bromo methyl-N-(2-cyano-phenyl)-benzenesulfonamide | 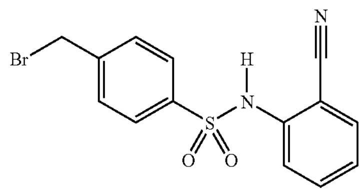 | MS (m/z): 349 (M − 1) |
| 39 | 3-Bromo methyl-N-(4-cyano-phenyl)-benzenesulfonamide | 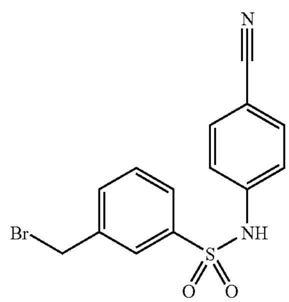 | MS (m/z): 350 (M − 1) |
| 40 | 3-Bromo methyl-N-(3-cyano-phenyl)-benzenesulfonamide | 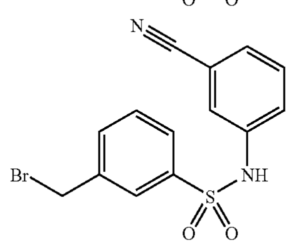 | MS (m/z): 350 (M − 1) |
| 41 | 3-Bromo methyl-N-(2-cyano-phenyl)-benzenesulfonamide | 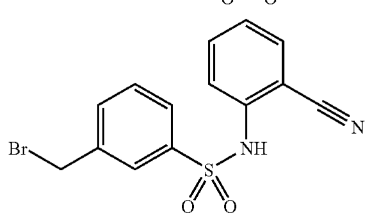 | MS (m/z): 350 (M − 1) |
| 42 | 4-(4-Bromo methyl-benzenesulfonylamino)-benzoic acid methyl ester | 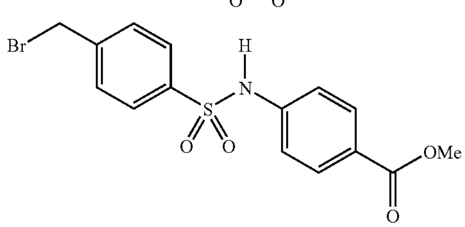 | MS (m/z): 383 (M − 1). |
| 43 | 3-(4-Bromo methyl-benzenesulfonylamino)-benzoic acid methyl ester | 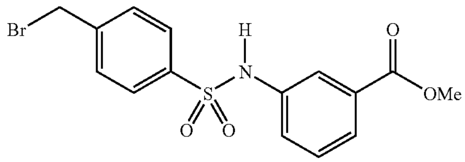 | MS (m/z): 383 (M − 1). |

Preparation 43

Synthesis of 4-(4-acetyl-3-hydroxy-2-propyl-phenoxymethyl)-N-(3-cyano-phenyl)-benzenesulfonamide Add 1-(2,4-dihydroxy-3-propyl-phenyl)-ethanone (2.77 g, 14.2 mmol) to sodium hydride (396 mg, 15.7 mmol) in dimethylformamide (20 mL) at 0° C., stir 10 minutes, add 4-bromomethyl-N-(3-cyano-phenyl)-benzenesulfonamide (2.50 g, 7.12 mmol) in dimethylformamide (15 mL) drop wise via addition funnel. After 2 hours at ambient temperature, pour into brine (40 mL), extract with ethyl acetate (2×40 mL), dry organic phase over sodium sulfate, filter and concentrate under reduced pressure. Purify residue by flash chromatography to yield the title compound (1.17 g, 2.52 mmol): MS (m/z): 463 (M−1).

The following compounds are prepared essentially by the method of Preparation 43.

| Prep. No. | Chemical name | Structure | Physical data |
|---|---|---|---|
| 44 | 4-(4-Acetyl-3-hydroxy-2-propyl-phenoxy methyl)-N-(4-cyano-phenyl)-benzenesulfonamide | 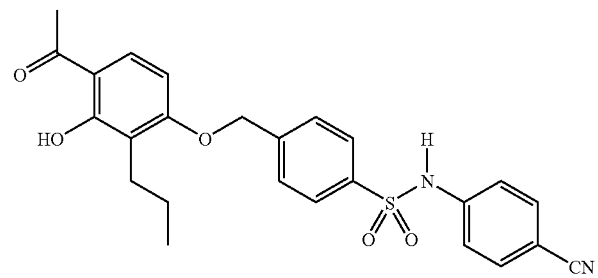 | MS (m/z): 463 (M − 1). |
| 45 | 4-(4-Acetyl-3-hydroxy-2-propyl-phenoxy methyl)-N-(2-cyano-phenyl)-benzenesulfonamide | 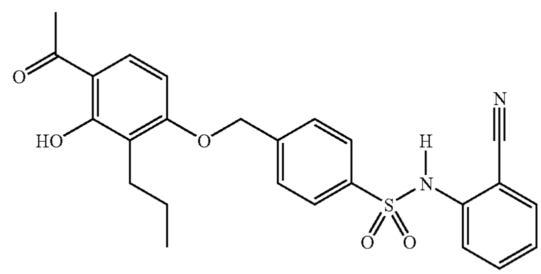 | MS (m/z): 463 (M − 1). |
| 46 | 3-(4-Acetyl-3-hydroxy-2-propyl-phenoxymethyl)-N-(4-cyano-phenyl)-benzenesulfonamide | 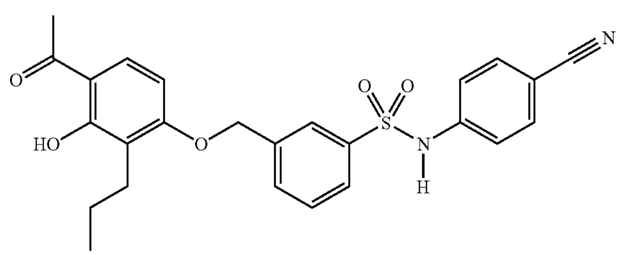 | MS (m/z): 463 (M − 1). |
| 47 | 3-(4-Acetyl-3-hydroxy-2-propyl-phenoxy methyl)-N-(3-cyano-phenyl)-benzenesulfonamide | 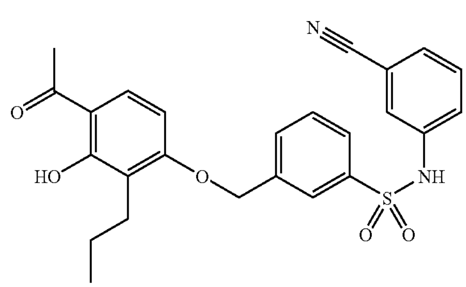 | MS (m/z): 463 (M − 1). |

| Prep. No. | Chemical name | Structure | Physical data |
|---|---|---|---|
| 48 | 3-(4-Acetyl-3-hydroxy-2-propyl-phenoxymethyl)-N-(2-cyano-phenyl)-benzenesulfonamide | 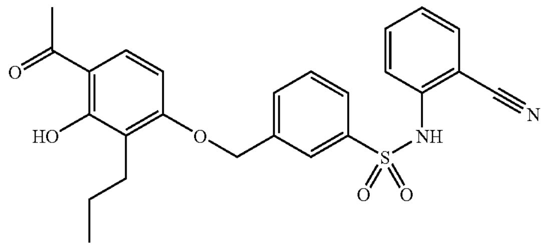 | MS (m/z): 463 (M − 1). |
| 49 | 4-[4-(4-Acetyl-3-hydroxy-2-propyl-phenoxy methyl)-benzenesulfonylamino]-benzoic acid methyl ester | 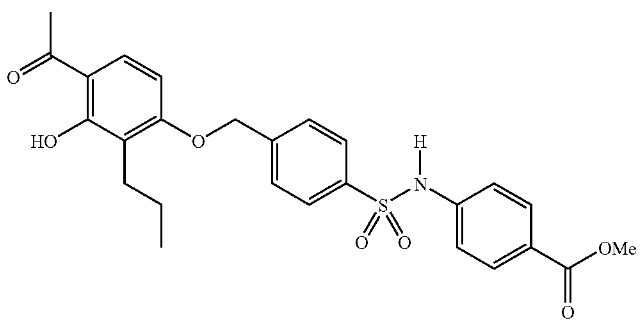 | MS (m/z): 496 (M − 1). |
| 50 | 3-[4-(4-Acetyl-3-hydroxy-2-propyl-phenoxy methyl)-benzenesulfonylamino]-benzoic acid methyl ester | 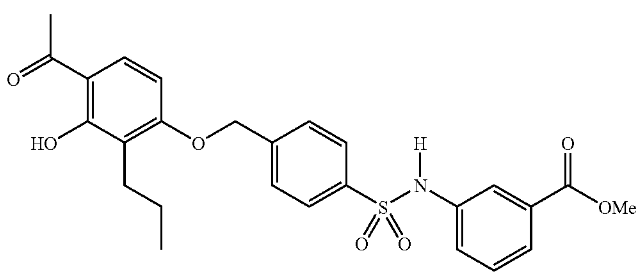 | MS (m/z): 496 (M − 1). |

Example 8

Synthesis of 4-(4-acetyl-3-hydroxy-2-propyl-phenoxymethyl)-N-[3-(2H-tetrazol-5-yl)-phenyl]-benzenesulfonamide

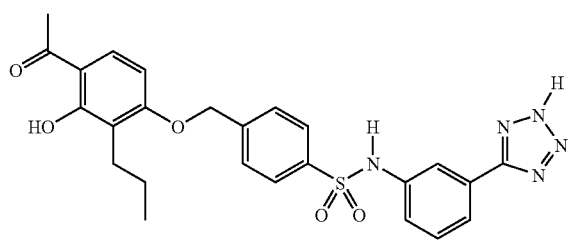

Combine 4-(4-acetyl-3-hydroxy-2-propyl-phenoxymethyl)-N-(4-cyano-phenyl)-benzenesulfonamide (1.44 g, 3.10 mmol), sodium azide (2.02 g, 31.0 mmol) and triethyl ammonium chloride (4.27 g, 31.0 mmol) in toluene (10.3 mL) and heat to reflux for 2 hours. Cool to ambient temperature and add 1N hydrochloric acid (20 mL) and ethyl acetate (20 mL). Extract the aqueous phase with ethyl acetate (2×20 mL), dry (sodium sulfate) and condense under reduced pressure. Sonicate resulting red residue in diethyl ether for 1 hour, collect the title compound by filtration as a white solid (831 mg, 1.64 mmol): $^1$H NMR (DMSO-$d_6$) δ 0.82 (t, 3H), 1.45 (m, 2H), 2.57 (m, 5H), 5.30 (s, 2H), 6.62 (d, 1H), 7.30 (m, 1H), 7.45 (t, 1H), 7.60 (m, 2H), 7.67 (m, 2H), 7.78 (d, 1H), 7.85 (m, 3H), 10.65 (s, 1H), 12.82 (s, 1H) tetrazole H not observed; MS (m/z): 506 (M−1). The following compounds are prepared essentially by the method of Example 8.

| Ex. # | Chemical name | Structure | Physical data |
|---|---|---|---|
| 9 | 4-(4-Acetyl-3-hydroxy-2-propyl-phenoxy methyl)-N-[4-(2 H-tetrazol-5-yl)-phenyl]-benzene-sulfonamide | 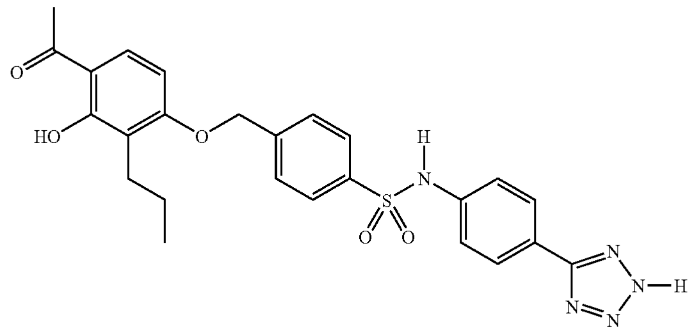 | $^1$H NMR (DMSO-d$_6$) δ 0.82 (t, 3 H), 1.45 (m, 2 H), 2.56 (m, 5 H), 5.30 (s, 2 H), 6.65 (d, 1 H), 7.40 (d, 2 H), 7.61 (d, 2 H), 7.79 (d, 1 H), 7.90 (m, 4 H), 10.70 (br s, 1 H), 12.82 (s, 1 H) tetrazole H not observed; MS (m/z): 506 (M − 1). |
| 10 | 4-(4-Acetyl-3-hydroxy-2-propyl-phenoxy methyl)-N-[2-(2 H-tetrazol-5-yl)-phenyl]-benzene-sulfonamide | 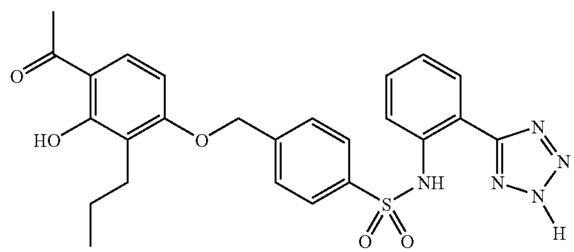 | $^1$H NMR (acetone-d$_6$) δ 0.89 (t, 3 H), 1.52 (m, 2 H), 2.57 (s, 3 H), 2.65 (m, 2 H), 5.29 (s, 2 H), 6.62 (d, 1 H), 7.28 (m, 2 H), 7.55 (m, 3 H), 7.76 (d, 2 H), 7.83 (m, 3 H), 8.03 (m, 1 H), 12.88 (s, 1 H); MS (m/z): 506 (M − 1). |
| 11 | 3-(4-Acetyl-3-hydroxy-2-propyl-phenoxy methyl)-N-[4-(2 H-tetrazol-5-yl)-phenyl]-benzene-sulfonamide | 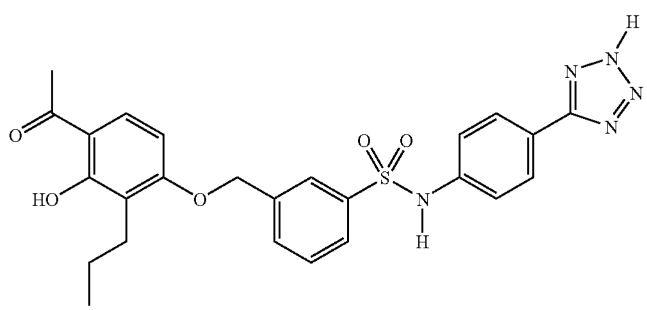 | $^1$H NMR (acetone-d$_6$) δ 0.91 (t, 3 H), 1.55 (m, 2 H), 2.56 (s, 3 H), 2.66 (m, 2 H), 5.35 (s, 2 H), 6.63 (d, 1 H), 7.44 (m, 2 H), 7.63 (t, 1 H), 7.75 (m, 2 H), 7.87 (m, 1 H), 8.00 (m, 2 H), 8.05 (m, 1 H), 9.50 (brs, 1 H), 12.88 (s, 1 H); MS (m/z): 506 (M − 1). |
| 12 | 3-(4-Acetyl-3-hydroxy-2-propyl-phenoxy methyl)-N-[3-(2 H-tetrazol-5-yl)-phenyl]-benzene-sulfonamide | 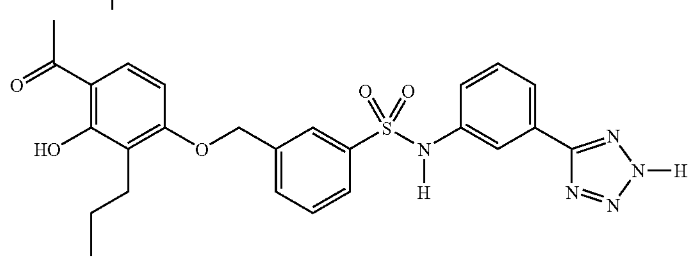 | $^1$H NMR (acetone-d$_6$) δ 0.88 (t, 3 H), 1.52 (m, 2 H), 2.58 (s, 3 H), 2.63 (m, 2 H), 5.32 (s, 2 H), 6.61 (d, 1 H), 7.41 (m, m), 7.46 (t, 1 H), 7.61 (t, 1 H), 7.73 (m, 2 H), 7.81 (m, 1 H), 7.85 (m, 1 H), 8.00 (m, 1 H), 8.03 (m, 1 H), 9.35 (br s, 1 H), 12.88 (s, 1 H); MS (m/z): 506 (M − 1). |
| 13 | 3-(4-Acetyl-3-hydroxy-2-propyl-phenoxy methyl)-N-[2-(2 H-tetrazol-5-yl)-phenyl]-benzene-sulfonamide | 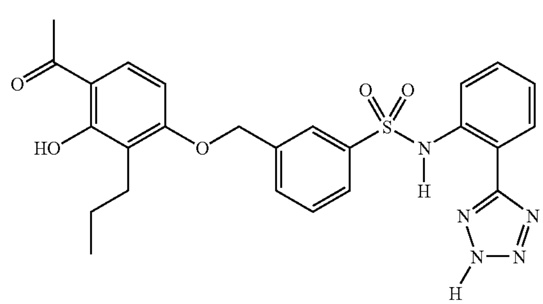 | $^1$H NMR (acetone-d$_6$) δ 0.91 (t, 3 H), 1.53 (m, 2 H), 2.58 (s, 3 H), 2.63 (m, 2 H), 5.27 (s, 2 H), 6.58 (d, 1 H), 7.27 (m, 1 H), 7.51 (t, 2 H), 7.68 (m, 1 H), 7.72 (d, 1 H), 7.76 (m, 1 H), 7.79 (m, 1 H), 7.96 (m, 1 H), 8.00 (m, 1 H), 12.88 (s, 1 H); MS (m/z): 506 (M − 1). |

Example 14

Synthesis of 4-[4-(4-acetyl-3-hydroxy-2-propyl-phenoxymethyl)-benzenesulfonylamino]-benzoic acid

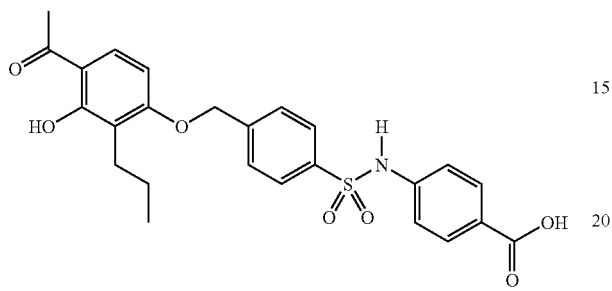

Dissolve 4-[4-(4-acetyl-3-hydroxy-2-propyl-phenoxymethyl)-benzenesulfonylamino]-benzoic acid methyl ester (1.48 g, 2.98 mmol) in methanol (15 mL) and add 2N aqueous lithium hydroxide solution (9 mL). Stir 24 hours. Concentrate under reduced pressure to remove majority of methanol, add 1N hydrochloric acid to the dark brown solution to afford a white precipitate. Triturate in 1N hydrochloric acid for 1 hour and collect the solid by filtration. Triturate the collected solid in 1:1 ether/hex and filter to collect the title compound as a white solid (1.102 g, 2.28 mmol): $^1$H NMR (DMSO-$d_6$) δ 0.85 (t, 3H), 1.46 (m, 2H), 2.58 (m, 5H), 5.30 (s, 2H), 6.65 (d, 1H), 7.20 (d, 2H), 7.61 (d, 2H), 7.80 (m, 3H), 7.87 (m, 2H), 10.82 (br s, 1H), 12.72 (br s, 1H), 12.82 (s, 1H); MS (m/z): 482 (M−1).

The following compound is prepared essentially by the method of Example 14.

Preparation 51

Synthesis of 3-bromomethyl-benzenesulfonyl chloride

Add N-bromosuccinimide (9.34 g, 52.5 mmol) and AIBN (5 mg, 0.32 mmol) to a solution of 3-methyl-benzenesulfonyl chloride (10.0 g, 52.5 mmol) in carbon tetrachloride (52 mL), and heat the solution at reflux for 12 hours. Filter the mixture to remove solids and condense under reduced pressure to afford a thick oil. Purify by flash chromatography to yield the title compound as an off-white crystalline solid (5.24 g, 19.4 mmol): $^1$H NMR (CDCl$_3$) δ 4.54 (s, 2H), 7.62 (m, 1H), 7.78 (m, 1H), 7.98 (m, 1H), 8.06 (m, 1H).

Example 16

Synthesis of sodium 3-[4-(4-acetyl-3-hydroxy-2-propyl-phenoxymethyl)-benzenesulfonylamino]-benzoate

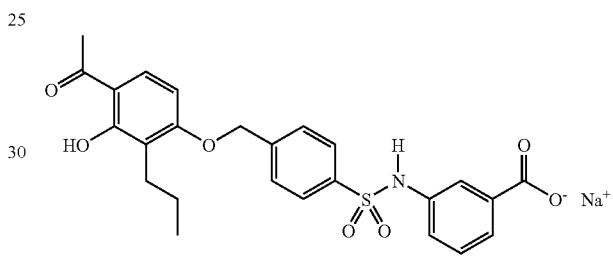

Stir 3-[4-(4-acetyl-3-hydroxy-2-propyl-phenoxymethyl)-benzenesulfonylamino]-benzoic acid (200 mg, 0.41 mmol) in ethyl acetate (10 mL) as a suspension. Add sodium 2-ethylhexanoate (92 mg, 0.90 mmol) in ethyl acetate (1 mL). After 12 hours at ambient temperature, concentrate the mixture under reduced pressure, sonicate the residue with ether (10 mL) and collect the title compound by filtration as a white solid (191 mg, 0.41 mmol): $^1$H NMR (DMSO-$d_6$) δ 0.85 (t, 3H), 1.48 (m, 2H), 2.58 (m, 5H), 5.30 (s, 2H), 6.62 (d, 1H), 7.08 (m, 2H), 7.40 (m, 1H), 7.53 (m, 3H), 7.78 (m, 3H), 12.82 (s, 1H); MS (m/z): 482. (M−1).

| Ex. # | Chemical name | Structure | Physical data |
|---|---|---|---|
| 15 | 3-[4-(4-Acetyl-3-hydroxy-2-propyl-phenoxy methyl)-benzenesulfonyl-amino]-benzoic acid | 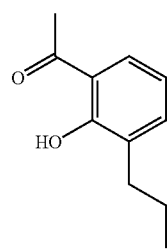 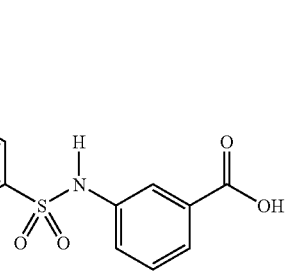 | $^1$H NMR (DMSO-$d_6$) δ 0.82 (t, 3 H), 1.45 (m, 2 H), 2.58 (m, 5 H), 5.30 (s, 2 H), 6.63 (d, 1 H), 7.35 (m, 2 H), 7.58 (m, 3 H), 7.68 (m, 1 H), 7.80 (m, 3 H), 10.53 br (s, 1 H), 12.82 (s, 1 H) 13.04 (br s, 1 H); MS (m/z): 482 (M − 1). |

The following compounds are prepared essentially by the method of Example 16.

| Ex. # | Chemical name | Structure | Physical data |
|---|---|---|---|
| 17 | Sodium; 4-(4-Acetyl-3-hydroxy-2-propyl-phenoxymethyl)-N-[3-(tetrazol-5-yl)-phenyl]-benzene-sulfonamide | 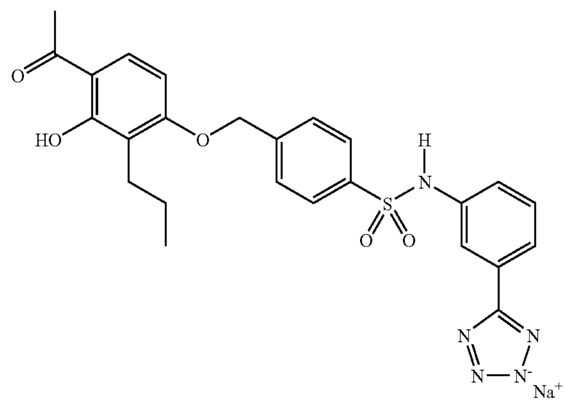 | $^1$H NMR (DMSO-d$_6$) δ 0.82(t, 3H), 1.45(m, 2H), 2.58(m, 5H), 5.30 (s, 2H), 6.60(d, 1H), 7.23(m, 1H), 7.56(m, 2H), 7.63(m, 1H), 7.78 (m, 4H), 10.30(s, 1H), 12.82(s, 1H); MS (m/z): 506(M−1). |
| 18 | Sodium; 4-(4-Acetyl-3-hydroxy-2-propyl-phenoxy-methyl)-N-[4-(tetrazolate-5-yl)-phenyl]-benzene-sulfonamide. | 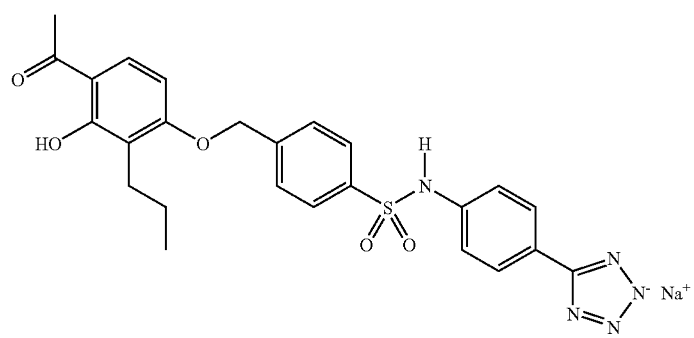 | $^1$H NMR (DMSO-d$_6$) δ 0.82(t, 3H), 1.48(m, 2H), 2.58(m, 5H), 5.30 (s, 2H), 6.62(d, 1H), 7.10(m, 2H), 7.58(m, 2H), 7.80(m, 5H), 10.22(br s, 1H), 12.82 (s, 1H); MS (m/z): 506 (M−1). |

Preparation 52

Synthesis of 6-(4-acetyl-3-hydroxy-2-propyl-phenoxymethyl)-pyridine-2-carboxylic acid methyl ester Combine 6-hydroxymethyl-pyridine-2-carboxylic acid methyl ester (2.20 g, 13.2 mmol), 1-(2,4-dihydroxy-3-propyl-phenyl)-ethanone (2.56 g, 13.2 mmol), and tri-n-butylphosphine (3.94 mL, 15.8 mmol) in THF (45 mL). Add diethyl diazodicarboxylate (3.98 g, 15.8 mmol). After 12 hours at ambient temperature, add diethyl ether (white precipitate forms) and filter, collect liquid and remove solvents under reduced pressure. Purify residue by flash chromatography eluting with 3:7 hexane:ethyl acetate to obtain the title compound as a white solid (3.769 g, 10.98 mmol): mass spectrum (m/e): 344 (M+1).

Preparation 53

Synthesis of 6-(4-acetyl-3-hydroxy-2-propyl-phenoxymethyl)-pyridine-2-carboxylic acid Dissolve 6-(4-acetyl-3-hydroxy-2-propyl-phenoxymethyl)-pyridine-2-carboxylic acid methyl ester (3.77 g, 10.9 mmol) in MeOH (20 mL) and water (5 mL). Add 2N aqueous lithium hydroxide (10.9 mmol). After 12 hours, concentrate under reduced pressure and dissolve the residue in 4N hydrochloric acid in dioxane. Add water until white precipitate forms and collect by filtration to yield the title compound as a white solid (2.30 g, 6.99 mmol): $^1$H NMR (d$_6$-DMSO) δ 0.89 (t, 3H), 1.50 (m, 2H), 2.56 (s, 3 H), 2.63 (t, 3H), 5.31 (s, 2H), 6.57 (d, 1H), 7.47 (m, 1H), 7.67 (d, 1H), 7.93 (m, 2H), 12.84 (s, 1H), (acid proton not observed); mass spectrum (m/e): 328 (M−1).

Preparation 54

Synthesis of 3-{[6-(4-acetyl-3-hydroxy-2-propyl-phenoxymethyl)-pyridine-2-carbonyl]-amino}-benzoic acid methyl ester Add one drop of dimethylformamide to a solution of 6-(4-acetyl-3-hydroxy-2-propyl-phenoxymethyl)-pyridine-2-carboxylic acid (800 mg, 2.43 mmol) and oxalyl chloride (0.23 mL, 2.67 mmol) in dichloromethane (24 mL) (gas evolution), stir 1 hour. Add a solution of methyl 3-aminobenzoate (365 mg, 2.43 mmol) and potassium carbonate (671 mg, 4.86 mmol) in acetone (16 mL). Stir resultant mixture for 16 hours. Dilute with dichloromethane (100 mL) and 1N hydrochloric acid (100 mL). Extract aqueous phase with dichloromethane, wash combined organic phase with saturated sodium bicarbonate solution. Dry organic phase over sodium sulfate and condense under reduced pressure. Triturate the residue in 1:1 acetone/diethyl ether. Dissolve resultant solid in ethyl acetate and wash with saturated sodium bicarbonate (2×), Dry organic phase over sodium sulfate and condense under reduced pressure to afford the title compound as a white solid (856 mg, 1.85 mmol). MS (m/z): 463 (M+1).

Example 19

Synthesis of 2-(4-acetyl-3-hydroxy-2-propyl-phenoxymethyl)-6-(3-carboxy-phenylcarbamoyl)-pyridine hydrochloride

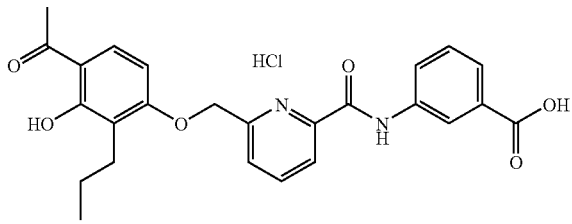

Dissolve 3-{[6-(4-acetyl-3-hydroxy-2-propyl-phenoxymethyl)-pyridine-2-carbonyl]-amino}-benzoic acid methyl ester (700 mg, 1.51 mmol) in minimal amount of tetrahydrofuran (2 mL), add methanol (8 mL), and 2N aqueous lithium hydroxide solution (2.27 mL, 4.54 mmol) and stir 30 hours. Add 1N hydrochloric acid (50 mL), collect resultant white solid by filtration to yield the title compound (493 mg, 1.02 mmol): $^1$H NMR (DMSO-$d_6$) δ 0.90 (t, 3H), 1.54 (m, 2H), 2.57 (s, 3H), 2.67 (m, 2H), 5.51 (s, 2H), 6.77 (d, 1H), 7.73 (m, 2H), 7.85 (d, 1H), 8.13 (m, 3H), 8.51 (m, 1H), 10.66 (s, 1H), 12.86 (s, 1H), 13.05 (br s, 1H): MS (m/z): 447 (M-HCl-1).

Preparation 55

Synthesis of 1-[2-hydroxy-4-(3-nitro-benzyloxy)-3-propyl-phenyl]-ethanone

Add 3-bromomethyl nitrobenzene (10.00 g, 46.3 mmol) to a solution of 1-(2,4-dihydroxy-3-propyl-phenyl)-ethanone (8.99 g, 46.3 mmol) in dimethylformamide (60 mL). After 10 minutes add potassium carbonate (9.60 g, 69.4 mmol) and cesium carbonate (15.08 g, 46.3 mmol). Stir at room temperature for one hour, then heat to 70° C. for 1.5 hours. Cool and add water (250 mL). Triturate for 15 minutes. Filter. Wash the solid with water several times, and then wash with hexanes. Dry to afford the title compound as an off white/light gray powder (12.9 g, 85%): $^1$H NMR (DMSO-$d_6$) δ 0.91 (t, 3H), 1.52 (m, 2H), 2.58 (s, 3H), 2.63 (m, 2H), 5.42 (s, 2H), 6.72 (d, 1H), 7.73 (t, 1H), 7.83 (d, 1H), 7.90 (d, 1H), 8.21 (d, 1H), 8.34 (s, 1H), 12.88 (bs, 1H).

The following compound is prepared essentially by the method of Preparation 55.

| Prep. No. | Chemical name | Structure | Physical data |
|---|---|---|---|
| 56 | 1-[2-Hydroxy-4-(2-nitro-benzyloxy)-3-propyl-phenyl]-ethanone | 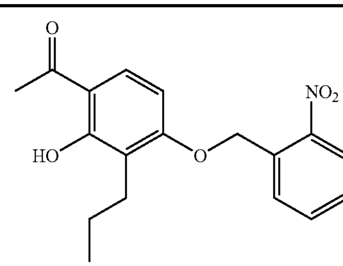 | $^1$H NMR (DMSO-$d_6$) δ 0.87 2.54 (t, 2 H), 2.58 (s, 3 H), 5.58 (s, 2 H), 6.72 (d, 1 H), 7.65 (t, 1 H), 7.76-7.85 (m, 3 H), 8.15 (d, 1 H), 12.86 (s, 1 H). |

Preparation 57

Synthesis of 1-[4-(3-amino-benzyloxy)-2-hydroxy-3-propyl-phenyl]-ethanone

Add zinc (21.6 g, 331 mmol) slowly to a solution of 1-[2-hydroxy-4-(3-nitro-benzyloxy)-3-propyl-phenyl]-ethanone (10.9 g, 6.07 mmol) in glacial acetic acid (120 mL). Stir the mixture for 3 hours. Dilute with dichloromethane (600 mL). Filter the reaction mixture through celite. Wash the celite pad several times with dichloromethane. Concentrate the combined filtrates. Partition the residue between ethyl acetate and saturated sodium bicarbonate. Wash the organic layer with brine, dry and concentrate to afford the title compound as a yellow solid (9.75 g, 98%): $^1$H NMR (CDCl$_3$) δ 0.96 (t, 3H), 1.58 (sextet, 2H), 2.54 (s, 3H), 2.71 (t, 2H), 5.07 (s, 2H), 6.46 (d, 1H), 6.62 (d, 1H), 6.71 (s, 1H), 6.78 (d, 1H), 7.16 (t, 1H), 7.54 (d, 1H), 12.75 (s, 1H).

The following compound is prepared essentially by the method of Preparation 57.

| Prep. No. | Chemical name | Structure | Physical data |
|---|---|---|---|
| 58 | 1-[4-(2-Amino-benzyloxy)-2-hydroxy-3-propyl-phenyl]-ethanone | | $^1$H NMR (CDCl$_3$) δ 0.92 (t, 3 H), 1.51 (sextet, 2 H), 2.57 (s, 3 H), 2.63 (t, 2 H), 5.10 (s, 2 H), 6.61 (d, 1 H), 6.73 (d, 1 H), 6.75 (t, 1 H), 7.15-7.21 (m, 2 H), 7.60 (d, 1 H), 12.74 (s, 1 H). |

Preparation 59

Synthesis of N-[3-(4-acetyl-3-hydroxy-2-propyl-phenoxymethyl)-phenyl]-3-cyano-benzamide Add a solution of 3-cyanobenzoyl chloride (553 mg, 3.34 mmol) in dichloromethane (10 mL) to a solution of 1-[4-(3-amino-benzyloxy)-2-hydroxy-3-propyl-phenyl]-ethanone (1.00 g, 3.34 mmol) in dichloromethane (10 mL), and triethyl amine (1.4 mL) at 0° C. Stir to room temperature for one hour. Partition the mixture between dichloromethane (20 mL) and 2N hydrochloric acid (30 mL). Wash the organic layer with 2N hydrochloric acid (20 mL), saturated sodium bicarbonate, brine, dry, filter, and concentrate to afford the title compound as a light yellow powder (1.33 g, 93%): $^1$H NMR (CDCl$_3$) δ 0.96 (t, 3H), 1.59 (sextet, 2H), 2.55 (s, 3H), 2.72 (t, 2H), 5.19 (s, 2H), 6.47 (d, 1H), 7.26 (d, 1H), 7.42 (t, 1H), 7.54-7.59 (m, 2H), 7.65 (t, 1H), 7.77 (s, 1H), 7.84 (d, 1H), 7.88 (s, 1H), 8.11 (d, 1H), 8.17 (s, 1H), 12.75 (s, 1H).

The following compounds are prepared essentially by the method of Preparation 59.

| Prep. No. | Chemical name | Structure | Physical data |
|---|---|---|---|
| 60 | N-[2-(4-Acetyl-3-hydroxy-2-propyl-phenoxymethyl)-phenyl]-3-cyano-benzamide | 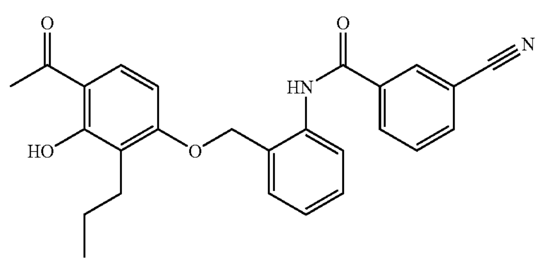 | $^1$H NMR (DMSO-d$_6$) δ 0.82 (t, 3 H), 1.42 (sextet, 2 H), 2.54 (t, 2 H), 2.56 (s, 3 H), 5.31 (s, 2 H), 6.63 (d, 1 H), 7.34 (t, 1 H), 7.40 (t, 1 H), 7.47 (d, 1 H), 7.53 (d, 1 H), 7.71-7.77 (m, 2 H), 8.07 (d, 1 H), 8.25 (d, 1 H), 8.36 (s, 1 H), 10.29 (s, 1 H), 12.84 (s, 1 H). |
| 61 | N-[3-(4-Acetyl-3-hydroxy-2-propyl-phenoxymethyl)-phenyl]-4-cyano-benzamide | 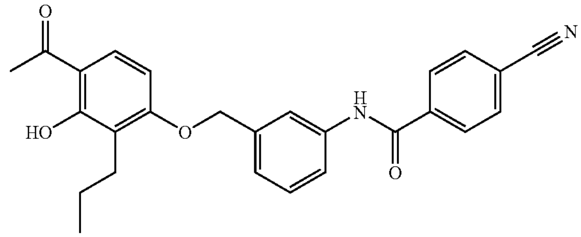 | $^1$H NMR (DMSO-d$_6$) δ 0.89 (t, 3 H), 1.51 (sextet, 2 H), 2.58 (s, 3 H), 2.62 (t, 2 H), 5.28 (s, 2 H), 6.74 (d, 1 H), 7.20 (d, 1 H), 7.41 (t, 1 H), 7.70 (d, 1 H), 7.81 (d, 1 H), 7.98 (s, 1 H), 8.14-8.21 (m, 4 H), 10.47 (s, 1 H), 12.85 (s, 1 H). |

Example 20

Synthesis of N-[3-(4-acetyl-3-hydroxy-2-propyl-phenoxymethyl)-phenyl]-3-(2H-tetrazol-5-yl)-benzamide

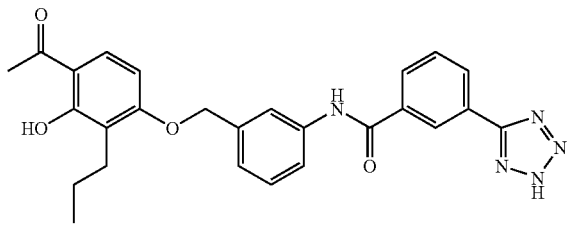

Heat a mixture of N-[3-(4-acetyl-3-hydroxy-2-propyl-phenoxymethyl)-phenyl]-3-cyano-benzamide (876 mg, 2.04 mmol), sodium azide (1.32 g, 20.4 mmol), and ammonium chloride (1.09 g, 20.4 mmol) in dimethylformamide (10 mL) at 110° C. overnight. Cool. Dilute with water (120 mL). Filter, and wash several times with water. Dry. Dissolve the residue in hot acetone (20 mL) and purify via chromatography, eluting with 1:1 hexanes:acetone with 1% acetic acid to afford the title compound as a light yellow powder (315 mg, 33%): $^1$H NMR (DMSO-$d_6$) δ 0.89 (t, 3H), 1.51 (sextet, 2H), 2.50 (s, 3H), 2.63 (t, 2H), 5.29 (s, 2H), 6.74 (d, 1H), 7.21 (d, 1H), 7.42 (t, 1H), 7.71 (d, 1H), 7.74 (t, 1H), 7.78 (d, 1H), 7.98 (s, 1H), 8.15 (d, 1H), 8.24 (d, 1H), 8.62 (s, 1H), 10.55 (s, 1H), 12.85 (s, 1H); MS (APCI-neg mode) m/z (rel intensity) 470 (100).

The following compounds are prepared essentially by the method of Example 20.

lamine (3.59 mL, 25.7 mmol) and stir at room temperature for 72 hours. At 5 hours, add additional methyl hydrogen isophthalate (200 mg). Stir overnight. Wash the mixture twice with 2N hydrochloric acid, saturated sodium bicarbonate, brine, dry, and concentrate. Triturate the residue with 1:1 hexanes: dichloromethane, and filter to afford the title compound as an off-white powder (1.83 g, 77%): $^1$H NMR (CDCl$_3$) δ 0.97 (t, 3H), 1.59 (sextet, 2H), 2.56 (s, 3H), 2.72 (t, 2H), 3.98 (s, 3H), 5.20 (s, 2H), 6.49 (d, 1H), 7.25 (m, 1H), 7.42 (t, 1H), 7.56-7.64 (m, 3H), 7.79 (s, 1H), 7.89 (s, 1H), 8.15 (d, 1H), 8.24 (d, 1H), 8.48 (s, 1H), 12.75 (s, 1H).

Example 22

Synthesis of N-[3-(4-acetyl-3-hydroxy-2-propyl-phenoxymethyl)-phenyl]-isophthalamic acid

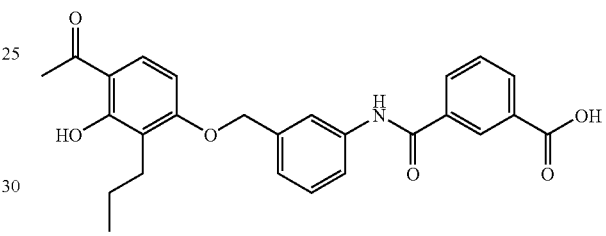

Add 1N lithium hydroxide (20 mL) to a solution of N-[3-(4-acetyl-3-hydroxy-2-propyl-phenoxymethyl)-phenyl]-isophthalamic acid methyl ester (1.75 g, 3.79 mmol) in tet-

| Ex.# | Chemical name | Structure | Physical data |
|---|---|---|---|
| 21 | N-[3-(4-Acetyl-3-hydroxy-2-propyl-phenoxymethyl)-phenyl]-4-(2 H-tetrazol-5-yl)-benzamide | (structure) | $^1$H NMR (DMSO-$d_6$) & 0.89 (t, 3 H), 1.51 (sextet, 2 H), 2.57 (s, 3 H), 2.63 (t, 2 H), 5.28 (s, 2 H), 6.74 (d, 1 H), 7.20 (d, 1 H), 7.41 (t, 1 H), 7.70 (d, 1 H), 7.98 (s, 1 H), 8.15 (d, 2 H), 8.19 (d, 2 H), 10.50 (s, 1 H), 12.85 (s, 1 H); MS (APCI-neg mode) m/z (rel intensity)470 (100). |

Preparation 62

Synthesis of N-[3-(4-acetyl-3-hydroxy-2-propyl-phenoxymethyl)-phenyl]-isophthalamic acid methyl ester Add ethyldimethylaminopropylcarbodiimide hydrochloride (2.47 g, 12.9 mmol) to a solution of 1-[4-(3-aminobenzyloxy)-2-hydroxy-3-propyl-phenyl]-ethanone (1.54 g, 5.14 mmol) and methyl hydrogen isophthalate (1.11 g, 6.17 mmol) in dichloromethane (40 mL) at 0° C. Add triethyrahydrofuran (15 mL) and ethanol (10 mL). Stir overnight at room temperature. Dilute with water. Acidify with 1N hydrochloric acid. Concentrate to remove organic solvents; filter and wash with water several times, then with hexanes. Dry to afford the title compound as an off-white powder (1.54 g, 91%): $^1$H NMR (DMSO-$d_6$) δ 0.89 (t, 3H), 1.51 (sextet, 2H), 2.58 (s, 3H), 2.63 (t, 2H), 5.27 (s, 2H), 6.74 (d, 1H), 7.20 (d, 1H), 7.40 (t, 1H), 7.65-7.71 (m, 2H), 7.81 (d, 1H), 7.97 (s, 1H), 8.14 (d, 1H), 8.18 (d, 1H), 8.52 (s, 1H), 10.51 (s, 1H), 12.85 (s, 1H), 13.43 (bs, 1H); MS (APCI-neg mode) m/z (rel intensity) 446 (100).

Example 23

Synthesis of N-[3-(4-acetyl-3-hydroxy-2-propyl-phenoxymethyl)-phenyl]-3-[(2,2-dimethyl-4,6-di-oxo-[1,3]dioxan-5-ylidene)-hydroxy-methyl]-benzamide

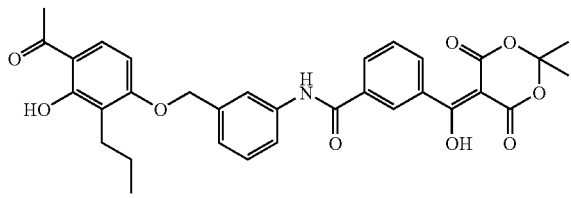

Add dicyclohexylcarbodiimide (0.231 g, 1.12 mmol, Aldrich Chemical Co.) to a solution of N-[3-(4-acetyl-3-hydroxy-2-propyl-phenoxymethyl)-phenyl]-isophthalamic acid (0.500 g, 1.12 mmol), 2,2-dimethyl-[1,3]dioxane-4,6-dione (0.161 g, 1.12 mmol), and 4-N,N-dimethylaminopyridine (0.273 g, 2.23 mmol, Chem-Impex) in dichloromethane (50 mL, 0.2 M). Filter precipitate, wash filter cake with dichloromethane, and concentrate filtrate. Dilute residue with dichloromethane and wash with 1N hydrochloric acid. Dry the organic layer with sodium sulfate and concentrate to afford the title compound (0.641 g, 1.12 mmol): MS (m/z): 572 (M−1).

Example 24

Synthesis of N-[3-(4-acetyl-3-hydroxy-2-propyl-phenoxymethyl)-phenyl]-3-[hydroxy-(1-methyl-2,4-dioxo-pyrrolidin-3-ylidene)-methyl]-benzamide

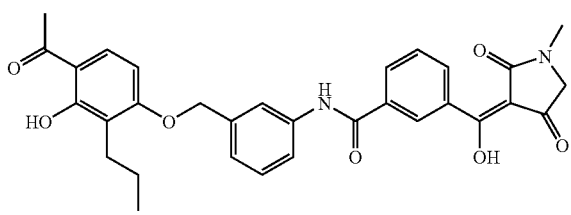

Add sarcosine methyl ester hydrochloride (0.156 g, 1.12 mmol) to a solution of N-[3-(4-acetyl-3-hydroxy-2-propyl-phenoxymethyl)-phenyl]-3-[(2,2-dimethyl-4,6-dioxo-[1,3]dioxan-5-ylidene)-hydroxy-methyl]-benzamide (0.641 g, 1.12 mmol) in toluene (0.2M). Add triethylamine (0.226 g, 2.23 mmol) and heat the solution at reflux for 24 h. Evaporate solvents and add potassium hydroxide (10 mmol) in 1:1 methanol/water (0.2M). Stir the reaction for 24 h. Precipitate product by diluting reaction mixture with water. Filter to afford the title compound (0.050 g, 0.092 mmol, 8%): $^1$H NMR (400 MHz, DMSO-$d_6$) δ 0.88 (t, J=7.0 Hz, 3H), 1.50 (q, J=9.8 Hz, 2H), 2.57 (s, 3H), 2.61 (t, J=7.2 Hz, 2H), 2.81 (s, 1H), 3.31 (m, 3H), 4.03 (s, 4H)(?), 5.25 (s, 2H), 6.72 (d, J=8.6 Hz, 1H), 7.17 (d, J=7.4 Hz, 1H), 7.37 (t, J=7.8 Hz, 1H), 7.46 (m, 1H), 7.68 (s, 2H), 7.80 (d, J=9.0 Hz, 1H), 7.95 (s, 2H), 8.05 (s, 1H), 10.31 (s, 1H), 12.84 (s, 1H). MS (m/z): 541 (M−1).

Preparation 63

Synthesis of N-[3-(4-acetyl-3-hydroxy-2-propyl-phenoxymethyl)-phenyl]-3-cyano-benzenesulfonamide Add 3-cyano-benzenesulfonyl chloride (673 mg, 3.34 mmol) to a solution of 1-[4-(3-amino-benzyloxy)-2-hydroxy-3-propyl-phenyl]-ethanone (1.00 g, 3.34 mmol) and pyridine (0.98 mL) in dichloromethane (20 mL) at 0° C. Warm to room temperature. Partition the mixture between dichloromethane and 2N hydrochloric acid (60 mL). Wash the organic layer with saturated sodium bicarbonate and brine. Dry and concentrate to afford the title compound as an orange solid (1.65 g): $^1$H NMR (DMSO-$d_6$) δ 0.85 (t, 3H), 1.47 (sextet, 2H), 2.55 (t, 2H), 2.57 (s, 3H), 5.19 (s, 2H), 6.62 (d, 1H), 7.05 (d, 1H), 7.14 (d, 1H), 7.23 (s, 1H), 7.29 (t, 1H), 7.73 (t, 1H), 7.77 (d, 1H), 7.98 (d, 1H), 8.07 (d, 1H) 8.12 (s, 1H), 10.55 (s, 1H), 12.86 (s, 1H).

Example 25

Synthesis of N-[3-(4-acetyl-3-hydroxy-2-propyl-phenoxymethyl)-phenyl]-3-(2H-tetrazol-5-yl)-benzenesulfonamide

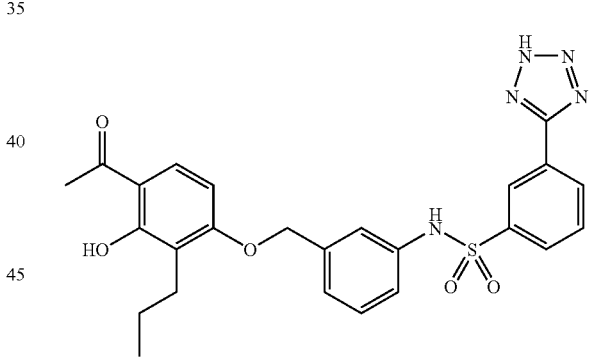

Heat a mixture of N-[3-(4-acetyl-3-hydroxy-2-propyl-phenoxymethyl)-phenyl]-3-cyano-benzenesulfonamide (1.00 g, 2.15 mmol), sodium azide (1.40 g, 21.5 mmol), and ammonium chloride (1.15 g, 21.5 mmol) in dimethylformamide (10 mL) at 110° C. overnight. Cool the reaction to room temperature and dilute with water (120 mL). Filter the resulting mixture, wash the filtered material several times with water and dry. Dissolve the residue in hot acetone (20 mL) and purify via chromatography, eluting with 1:1 hexanes:acetone with 1% acetic acid to afford the title compound as a tan solid (490 mg, 45%): $^1$H NMR (DMSO-$d_6$) δ 0.80 (t, 3H), 1.42 (sextet, 2H), 2.49 (s, 3H), 2.50 (t, 2H), 5.16 (s, 2H), 6.59 (d, 1H), 7.10 (d, 1H), 7.12 (d, 1H), 7.24 (s, 1H), 7.25 (t, 1H), 7.70 (d, 1H), 7.73 (t, 1H), 7.87 (d, 1H), 8.22 (d, 1H), 8.49 (s, 1H), 10.56 (s, 1H), 12.82 (s, 1H); MS (APCI-neg mode) m/z (rel intensity) 506 (100).

We claim:
1. A compound of formula I wherein
R¹ is selected from the group consisting of C1-C5 alkyl, C3-C7 cycloalkyl, C4-C8 cycloalkylalkyl, phenyl and substituted phenyl;
R² is selected from the group consisting of hydrogen, C1-C5 alkyl, substituted C1-C5 alkyl, halo, phenyl, substituted phenyl, C1-C3 fluoroalkyl, CN, $CO_2R^3$, thiophenyl, substituted thiophenyl, thiazolyl, substituted thiazoyl, furanyl, substituted furanyl, pyridinyl, substituted pyridinyl, oxazolyl, substituted oxazloyl, isothiazolyl, substituted isothiazoyl, isoxazolyl, substituted isoxazolyl, 1,2,4-oxadiazolyl, substituted 1,2,4-oxadiazolyl, pyrimidinyl, substituted pyrimidinyl, pyridazinyl, and substituted pyridazinyl;
X is selected from the group consisting of O, $S(O)_m$, and $NR^3$;
Y is selected from the group consisting of C1-C3 alkanediyl and substituted C1-C3 alkanediyl;
$Ar_1$ and $Ar_2$ are independently selected from the group consisting of phenylene, substituted phenylene, thiophenediyl, substituted thiophenediyl, thiazolediyl, substituted thiazolediyl, furanediyl, substituted furanediyl, pyridinediyl, substituted pyridinediyl, oxazolediyl, substituted oxazolediyl, isothiazolediyl, substituted isothiazolediyl, isoxazolediyl, substituted isoxazolediyl, pyrimidinediyl, substituted pyrimidinediyl, pyridazinediyl, substituted pyridazinediyl and 1,2,4-oxadiazole-3,5-diyl;
L is —SO₂NH—;
R³ is independently hydrogen or C1-C5 alkyl;
Z is selected from the group consisting of $(CH_2)_n COOH$, -continued m is 0, 1, or 2;
n and q are independently 0, 1, 2 or 3;
and pharmaceutically acceptable salts thereof.

2. The compound according to claim 1 wherein X is O.

3. The compound according to claim 2 wherein Y is C1-C3 alkanediyl.

4. The compound according to claim 3 wherein $Ar_1$ and $Ar_2$ are independently phenylene or pyridinediyl.

5. The compound according to claim 4 wherein R² is C1-C5 alkyl.

6. The compound according to claim 1 wherein
X is O;
Y is C1-C3 alkanediyl;
$Ar_1$ and $Ar_2$ are independently phenylene or pyridinediyl;
R² is C1-C5 alkyl;
L is —SO₂NH;
Z is selected from the group consisting of $(CH_2)_n COOH$ and and
n and q are 0.

7. The compound according to claim 6 wherein $Ar_1$ is phenylene.

8. The compound according to claim 7 wherein $Ar_2$ is phenylene.

9. The compound according to claim 8 wherein $Ar_2$ is attached at the 1-4 position.

10. The compound according to claim 8 wherein $Ar_2$ is attached at the 1-3 position.

11. The compound according to claim 9 or claim 10 wherein Ar₁ is attached at the 1-3 position or 1-4 position.

12. The compound according to claim 6 wherein $R^1$ is methyl.

13. The compound according to claim 1 wherein
$R^1$ methyl;
$R^2$ is propyl;
X is O;
Y is methylene;
Ar₁ is phenylene or pyridinediyl;
Ar₂ is phenylene or fluorophenylene;
L is —SO₂NH;
Z is selected from the group consisting of $(CH_2)_n COOH$,

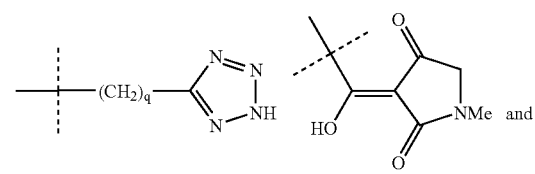

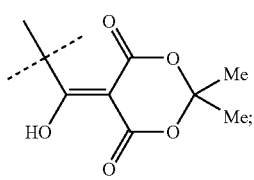

n is 0 or 1; and
q is 0.

14. The compound according to claim 1 which is 4-(4-acetyl-3-hydroxy-2-propyl-phenoxymethyl)-N-[2-(2H-tetrazol-5-yl)-phenyl]-benzenesulfonamide.

15. A pharmaceutical composition comprising a compound of claim 1 and a pharmaceutically acceptable carrier, diluent or excipient.

16. A method of treating migraine, comprising administering to a patient in need thereof an effective amount of a compound of claim 1.

17. A process for preparing the compound of formula I, or a pharmaceutically acceptable salt thereof, wherein $R^1$, $R^2$, X, Y, Ar₁, L and Ar₂ are defined as in claim 1 comprising the step selected from
(A) for a compound of formula I where Z is tetrazolyl,

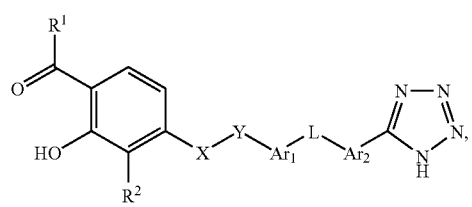

Z is tetrazolyl
cycloaddition of a compound of formula II where $R^{10}$ is cyano with an azide reagent,

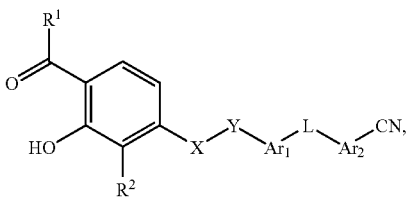

$R^{10}$ is cyano
(B) for a compound of formula I where Z is COOH,

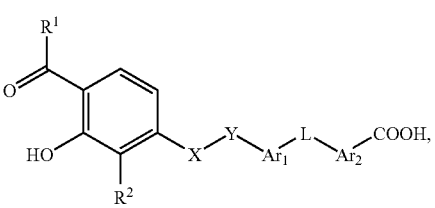

Z is COOH
hydrolysis of a compound of formula II wherein $R^{10}$ is $COOR^{14}$ and $R^{14}$ is selected from the group consisting of C1-C5 alkyl, phenyl and benzyl;

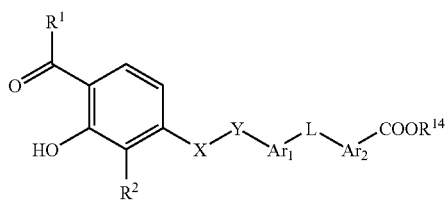

and
(C) for a compound of formula I where Z is COOH,

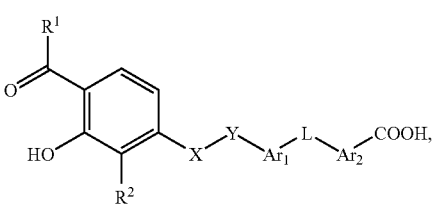

Z is COOH hydrolysis of a compound of formula II where $R^{10}$ is cyano;

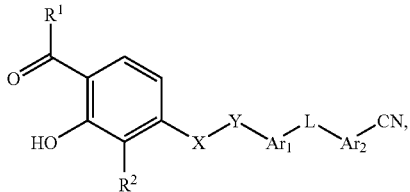

II $R^{10}$ is cyano;

whereafter, when a pharmaceutically acceptable salt of the compound of formula I is required, it is obtained by reacting the acid of formula I with a physiologically acceptable base or by reacting a basic compound of formula I with a physiologically acceptable acid or by any other conventional procedure.

18. A compound of formula II

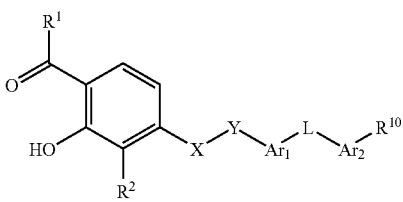

II wherein
  $R^1$, $R^2$, X, Y, $Ar_1$, $Ar_2$ and L are defined as in claim 1;
  $R^{10}$ is CN or $COOR^{14}$; and $R^{14}$ is selected from the group consisting of C1-C5 alkyl, phenyl and benzyl.

19. A compound according to claim 18 wherein $R^{14}$ is methyl.

* * * * *